(12) United States Patent
Schwarz et al.

(10) Patent No.: US 8,513,260 B2
(45) Date of Patent: Aug. 20, 2013

(54) PYRAZINYLPYRAZOLES

(75) Inventors: Hans-Georg Schwarz, Dorsten (DE); Jens Frackenpohl, Frankfurt (DE); Achim Hense, Leverkusen (DE); Simon Maechling, Köln (DE); Stefan Schnatterer, Hattersheim (DE); Robert Velten, Langenfeld (DE); Stefan Werner, Monheim (DE); Angela Becker, Düsseldorf (DE); Olga Malsam, Rösrath (DE); Eva-Maria Franken, Lyons (FR); Arnd Voerste, Köln (DE); Ulrich Görgens, Ratingen (DE); Peter Lümmen, Idstein (DE)

(73) Assignee: Bayer CropScience AG, Monheim (DE)

( * ) Notice: Subject to any disclaimer, the term of this patent is extended or adjusted under 35 U.S.C. 154(b) by 255 days.

(21) Appl. No.: 12/801,253

(22) Filed: May 28, 2010

(65) Prior Publication Data
US 2011/0021539 A1 Jan. 27, 2011

(30) Foreign Application Priority Data
May 29, 2009 (EP) .................................. 09161568

(51) Int. Cl.
*A01N 25/26* (2006.01)
(52) U.S. Cl.
USPC ....... 514/255.05; 544/405; 504/100; 504/235
(58) Field of Classification Search
USPC .................................. 544/405; 514/255.05
See application file for complete search history.

(56) References Cited

U.S. PATENT DOCUMENTS

| | | | |
|---|---|---|---|
| 3,041,342 | A | 6/1962 | Jucker et al. |
| 4,101,540 | A | 7/1978 | Coispeau |
| 6,169,086 | B1 | 1/2001 | Ejima et al. |
| 2006/0014802 | A1 | 1/2006 | Billen et al. |
| 2010/0144672 | A1 | 6/2010 | Frackenpohl et al. |
| 2011/0124660 | A1* | 5/2011 | Schwarz et al. ......... 514/255.05 |

FOREIGN PATENT DOCUMENTS

| | | |
|---|---|---|
| DE | 26 43 640 A1 | 4/1977 |
| DE | 195 44 799 A1 | 6/1997 |
| JP | 08-208620 A | 8/1996 |
| WO | WO 98/32739 A1 | 7/1998 |
| WO | WO 99/64428 A1 | 12/1999 |
| WO | WO 01/07413 A1 | 2/2001 |
| WO | WO 2007/027842 A1 | 3/2007 |
| WO | WO 2007/048733 A1 | 5/2007 |
| WO | WO 2008/077483 A1 | 7/2008 |

OTHER PUBLICATIONS

Aggarwal, R., et al., "Synthesis and antibacterial activity of some new 1-heteroaryl-5-amino-3*H*/methyl-4-phenylpyrazoles," *Bioorganic & Medicinal Chemistry 14*:1785-1791, Elsevier Ltd., England (2006).

Britsun, V.N., et al., "Synthesis and structural determination of 5-arylamino-1,3-dimethylpyrazoles," *Chemistry of Heterocyclic Compounds 41*: 105-110, Springer Science+Business Media, Inc., United States (2005).

Chen, C., et al., "Optimization of 3-phenylpyrazolo[1,5-*a*]pyrimidines as potent corticotropin-releasing factor-1 antagonists with adequate lipophilicity and water solubility," *Bioorganic & Medicinal Chemistry Letters 14*:3669-3673, Elsevier Ltd., England (2004).

DeWald, H.A., et al., "Pyrazolodiazepines. 2. 4-Aryl-1,3-dialkyl-6,8-dihydropyrazolo[3,4-*e*][1,4]diazepin-7(1*H*)-ones as Antianxiety and Anticonvulsant Agents," *Journal of Medicinal Chemistry 20*:1562-1569, American Chemical Society, United States (1977).

Ducray, R., et al., "Novel 3-alkoxy-1*H*-pyrazolo[3,4-*d*]pyrimodines as EGFR and erbB2 receptor tyrosine kinase inhibitors," *Bioorganic & Medicinal Chemistry Letters 18*: 959-962, Elsevier Ltd., England (2008).

Elhaïk, J., et al., "The spin-states and spin-crossover behaviour of iron(II) complexes of 2,6-dipyrazol-1-ylpyrazine derivatives," *Dalton Transactions 10*:2053-2060, The Royal Society of Chemistry, England (2003).

Gilligan, P.J., et al., "The Discovery of 4-(3-Pentylamino)-2,7-dimethyl-8-(2-methyl-4-methoxyphenyl)-pyrazolo-[1,5-*a*]-pyrimidine: A Corticotropin-Releasing Factor (hCRF$_1$) Antagonist" *Bioorganic & Medicinal Chemistry 8*:181-189, Elsevier Science Ltd., England (2000).

Karpeisky, A., et al., "Scaleable and efficient synthesis of 2'-deoxy-2'-*N*-phthaloyl nucleoside phosphoramidites for oligonucleotide synthesis," *Bioorganic & Medicinal Chemistry Letters 12*:3345-3347, Elsevier Science Ltd., England (2002).

Kumar, V., et al., "Synthesis and antibacterial activity of some new 1-heteroaryl-5-amino-4-phenyl-3-trifluoromethylpyrazoles," *European Journal of Medicinal Chemistry 40*: 922-927, Elsevier SAS, England (2005).

Nes, W.R. and Burger, A., "Amine and Enol Derivatives of 1,1,1-Trifluoropropane," *J. Am. Chem. Soc. 72*: 5409-5413, American Chemical Society, United States (1950).

(Continued)

*Primary Examiner* — Susanna Moore
(74) *Attorney, Agent, or Firm* — Sterne, Kessler, Goldstein & Fox P.L.L.C.

(57) ABSTRACT

Pyrazin-2-ylpyrazoles of formula (I)

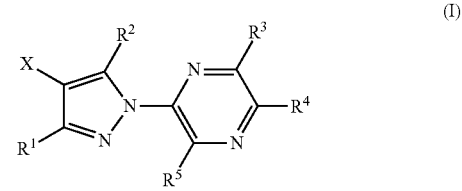

in which X, $R^1$, $R_2$, $R^3$, $R^4$, and $R^5$ are as defined in the description are described, as is the use thereof as insecticides and/or parasiticides, the preparation thereof, and compositions which comprise such pyrazin-2-ylpyrazoles.

16 Claims, No Drawings

(56) References Cited

OTHER PUBLICATIONS

Steel, P.J. and Constable, E.C., "Syntheses of new pyrazole-derived chelating ligands," *Journal of Chemical Chemistry Research* 7:1601-1611, The Royal Society of Chemistry, England (1989).

Esp@cenet database, European Patent Office, English language abstract of German Patent Publication No. DE 195 44 799 A1, published Jun. 5, 1997.

Esp@cenet database, European Patent Office, English language abstract for Japanese Patent Publication No. JP 08-208620 A, published Aug. 13, 1996.

Office Action mailed Feb. 12, 2013, in the U.S. Appl. No. 13/375,164, Schwartz et al., Int'l Filing Date: May 19, 2010, U.S. Patent and Trademark Office.

\* cited by examiner

PYRAZINYLPYRAZOLES

The present invention relates to pyrazin-2-ylpyrazoles, and to the use thereof as insecticides and/or parasiticides.

The present invention further provides processes for preparation thereof, and compositions which comprise such pyrazin-2-ylpyrazoles.

WO 2007/048733 A describes the use of aminopyrazoles for controlling phytopathogenic harmful fungi, which also encompass pyrazin-2-ylpyrazoles in a generic manner. The pyrazin-2-ylpyrazoles bear only hydrogen as a substituent in the 3 position.

WO 2007/027842 A discloses anilinopyrazoles which may be substituted in the 1 position of the pyrazole unit by 2-pyrazines. This international application relates to pharmaceutical applications, more particularly to the treatment of diabetes; no arthropodicidal effect is described.

The active ingredients already known according to the documents cited above have disadvantages in the use thereof, more particularly that they have only inadequate insecticidal action, if any. There is therefore a need further insecticides and/or parasiticides.

It is therefore an object of the present invention to provide alternative insecticides and/or parasiticides which exhibit improved action or a broader spectrum of activity compared to the active ingredients known from the prior art.

This object is achieved by pyrazinylpyrazoles of the general formula (I)

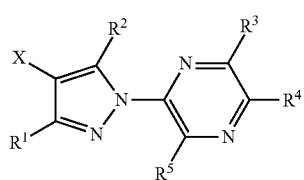

(I)

in which

X is phenyl, 2-pyridyl or 3-pyridyl, each of which is substituted by one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH=NO—H, —CH=NO-alkyl, —CH=NO-halolkyl, —C(CH$_3$)=NO—H, —C(CH$_3$)=NO-alkyl, —C(CH$_3$)=NO-haloalkyl; or phenyl, 2-pyridyl and 3-pyridyl optionally substituted by one or more halogen atoms, cyano, nitro, alkyl, alkoxy or haloalkyl, where vicinal alkyl, haloalkyl, alkoxy and/or haloalkoxy groups on the phenyl substituent, 2-pyridyl substituent or 3-pyridyl substituent, together with the carbon atoms to which they are bonded, may form a five- to seven-membered cyclic system which contains 0 to 2 oxygen or nitrogen atoms, where no two oxygen atoms are directly bonded to one another, and the alkyl moiety of which may optionally be substituted by one or more halogen atoms and/or further alkyl radicals;

R$^1$ is hydrogen, alkyl which is optionally mono- or independently polysubstituted by alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl and/or cycloalkyl; alkenyl which is optionally mono- or independently polysubstituted by halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and/or cycloalkyl; cycloalkyl which is optionally mono- or independently polysubstituted by alkyl, haloalkyl and/or halogen; haloalkyl which is optionally mono- or independently polysubstituted by alkoxy, alkylsulphanyl, haloalkylsulphanyl, alkylsulphinyl, haloalkylsulphinyl, alkylsulphonyl, haloalkylsulphonyl and/or phenyl optionally mono- or independently polysubstituted by halogen, alkyl, haloalkyl and/or alkoxy; phenyl which is optionally mono- or independently polysubstituted by halogen, alkyl, haloalkyl and/or alkoxy; benzyl which is optionally mono- or independently polysubstituted by halogen, alkyl, haloalkyl and/or alkoxy; cyano, formyl, alkylcarbonyl, —CH=NO—H, —CH=NO-alkyl, —CH=NO-haloalkyl, —C(CH$_3$)=NO—H, —C(CH$_3$)=NO-alkyl or —C(CH$_3$)=NO-haloalkyl;

R$^2$ is optionally substituted amino, where amino may be mono- or independently disubstituted by alkyl, haloalkyl, alkoxyalkyl, alkylsulphanylalkyl, alkylsulphinylalkyl, alkylsulphonylalkyl, alkylcarbonyl, cycloalkyl, cycloalkylalkyl, alkenyl, where the above radicals are optionally substituted by halogen, cyano, alkoxy, alkoxycarbonyl or phenyl, where the phenyl ring is optionally mono- or polysubstituted by one or more substituents selected independently from halogen, alkyl, haloalkyl and alkoxy; alkynyl, alkoxycarbonyl, alkenyloxycarbonyl, alkynyloxycarbonyl, alkoxycarbonylalkyl, alkoxycarbonylcarbonyl, heterocyclyl, heteroaryl, heterocyclylalkyl or heteroarylalkyl, where the heterocyclic or heteroaromatic ring may optionally be mono- or polysubstituted by one or more substituents selected independently from halogen, alkyl, haloalkyl and alkoxy; benzyl or phenylcarbonyl, where the phenyl ring in the benzyl and phenylcarbonyl is optionally mono- or polysubstituted by one or more substituents selected independently from halogen, alkyl, haloalkyl and alkoxy; and R$^3$, R$^4$ are each independently hydrogen, halogen, alkyl, cycloalkyl, haloalkyl, cyano, hydroxyl, formyl, alkylcarbonyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl, nitro, hydroxyl, SH, alkoxy, alkylsulphanyl, haloalkylsulphanyl, alkylsulphinyl, haloalkylsulphinyl, alkylsulphonyl or haloalkylsulphonyl;

R$^5$ is halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, —SH, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, nitro, amino, alkylamino, dialkylamino, alkylsulphonylamino, dialkylsulphonylamino, formyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl or heteroaryl, where the heteroaromatic ring may optionally be mono- or polysubstituted by one or more substituents selected independently from halogen, alkyl, haloalkyl and alkoxy;

and the N-oxides and salts of the compounds of the general formula (I).

It has been found in accordance with the invention that the compounds of the general formula (I) and the N-oxides and salts thereof possess good insecticidal and parasiticidal properties and can be used in crop protection, in the animal health and materials protection sector, more particularly for protection of industrial materials to control unwanted pests, such as insects, spider mites, endo- or ectoparasites.

Preferred embodiments of the compounds of the general formula (I) are described hereinafter.

In a first embodiment of the present invention,
(a) preferred compounds of the formula (I) are those in which the X radical is phenyl, 2-pyridyl or 3-pyridyl, each of which is substituted by one or more substituents selected from the group consisting of halogen, alkyl, haloalkyl, alkoxy, haloalkoxy, alkylsulphanyl, haloalkylsulphanyl, alkylsulphinyl, haloalkylsulphinyl, alkylsulphonyl, haloalkylsulphonyl, cyano, nitro and dialkylamino; or phenyl, 2-pyridyl and 3-pyridyl optionally substituted by one or more halogen atoms, cyano, nitro, alkyl, alkoxy or haloalkyl, where vicinal alkyl, haloalkyl and/or alkoxy groups on the phenyl substituent, 2-pyridyl substituent or 3-pyridyl substituent, together with the carbon atoms to which they are bonded, may form a five- to seven-membered cyclic system which contains 0 to 2 oxygen or nitrogen atoms, where no two oxygen atoms are directly bonded to one another, and the alkyl moiety thereof may optionally be substituted by one or more halogen atoms and/or further alkyl radicals;
(b) more preferred compounds of the formula (I) are those in which the X radical is phenyl, 2-pyridyl or 3-pyridyl, each of which is substituted by one or more substituents selected from the group consisting of halogen, alkyl, haloalkyl, alkoxy, haloalkoxy, alkylsulphanyl, haloalkylsulphanyl, alkylsulphinyl, haloalkylsulphinyl, alkylsulphonyl, haloalkylsulphonyl, cyano and dialkylamino; or phenyl, 2-pyridyl and 3-pyridyl optionally substituted by one or more halogen atoms, cyano, nitro, alkyl, alkoxy or haloalkyl, where vicinal alkyl, haloalkyl and/or alkoxy groups on the phenyl substituent, 2-pyridyl substituent or 3-pyridyl substituent, together with the carbon atoms to which they are bonded, may form a five- to seven-membered cyclic system which contains 1 to 2 oxygen atoms, where no two oxygen atoms are directly bonded to one another, and the alkyl moiety thereof may optionally be substituted by one or more halogen atoms and/or further alkyl radicals;
(c) especially preferred compounds of the formula (I) are those in which the X radical is phenyl, 2-pyridyl or 3-pyridyl, each of which is substituted by one or more substituents selected from the group consisting of fluorine, chlorine, bromine, iodine, $CF_3$, methoxy, ethoxy, propoxy, trifluoroethoxy, methylsulphanyl, 2,2,2-trifluoroethylsulphanyl, methylsulphinyl, 2,2,2-trifluoroethylsulphinyl, methylsulphonyl, 2,2,2-trifluoroethylsulphonyl, cyano and dimethylamino; or phenyl optionally substituted by one or more halogen atoms, cyano, nitro, methyl, methoxy or $CF_3$, where vicinal alkyl or alkoxy groups on the phenyl substituent, together with the carbon atom to which they are bonded, may form a five- to seven-membered cyclic system which contains 1 or 2 oxygen atoms, where no two oxygen atoms are directly bonded to one another, and the alkyl moiety thereof may be substituted by one or more further alkyl radicals;

In a second embodiment of the present invention,
(a) preferred compounds of the formula (I) are those in which the $R^1$ radical is hydrogen, alkyl which is optionally mono- or polysubstituted by alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl and/or cycloalkyl; alkenyl which is optionally mono- or polysubstituted by halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and/or cycloalkyl; cycloalkyl which is optionally mono- or polysubstituted by alkyl, haloalkyl and/or halogen; haloalkyl which is optionally mono- or polysubstituted by alkoxy, alkylsulphonyl, haloalkylsulphanyl, alkylsulphinyl, haloalkylsulphinyl, alkylsulphonyl, haloalkylsulphonyl and/or phenyl; CH=NOH, CH=NOCH$_3$ or CN;
(b) more preferred compounds of the formula (I) are those in which the $R^1$ radical is alkyl which is optionally mono- or polysubstituted by alkoxy; alkenyl which is optionally mono- or polysubstituted by halogen; cycloalkyl which is optionally mono- or polysubstituted by alkyl, haloalkyl and/or halogen; haloalkyl which is optionally mono- or polysubstituted by alkoxy; CH=NOH, CH=NOCH$_3$ or CN;
(c) especially preferred compounds of the formula (I) are those in which the $R^1$ radical is $CH_3$, $CH_2CH_3$, $CH(CH_3)_2$, $CH_2CH_2CH_3$, $C(CH_3)_3$, $C(OCH_3)HCH_2CH_3$, $CH(OCH_3)_2$, CH=CH$_2$, prop-1-en-2-yl, cyclopropyl, $CF_3$, CHFCH$_3$, CHF$_2$, $CF_2Cl$, $CF_2Br$, $CF_2CF_3$, $CF_2CH_3$, $CF_2CF_2CF_3$, $CF_2CF_2H$, 2-fluoropropan-2-yl, 1,1,2,2 tetrafluoro-2-methoxyethyl, CH=NOH, CH=NOCH$_3$ or CN, In a third embodiment of the present invention, preferred compounds of the general formula (I) are those in which the $R^2$ radical is amino and substituted amino, where the substituted amino may be mono- or independently disubstituted by alkyl, haloalkyl, cycloalkylalkyl, optionally halogen- or phenyl-substituted alkenyl, alkynyl, heterocyclylalkyl and/or heteroarylalkyl, where the heteroaromatic ring may optionally be mono- or polysubstituted by one or more substituents selected independently from halogen, alkyl, haloalkyl and alkoxy; benzyl, where the phenyl ring in the benzyl may optionally be mono- or polysubstituted by one or more substituents selected independently from halogen, alkyl, haloalkyl and alkoxy,
(a) more preferred compounds of the formula (1) are those in which the $R^2$ radical is amino or substituted amino, where the substituted amino may be mono- or independently disubstituted by alkyl, optionally halogen- or phenyl-substituted alkenyl, alkynyl, heteroarylalkyl, where the heteroaromatic ring may optionally be mono- or polysubstituted by one or more substituents selected independently from halogen and/or alkyl; benzyl, where the phenyl ring in the benzyl may optionally be mono- or polysubstituted by one or more substituents selected independently from halogen and alkoxy,
(b) especially preferred compounds of the formula (1) are those in which the $R^2$ radical is amino, methylamino, dimethylamino, benzylamino, dibenzylamino, (4-chlorobenzyl)amino, bis(4-chlorobenzyl)amino, (4-methoxybenzyl)amino, bis(4-methoxybenzyl)amino, (2-methylprop-2-en-1-yl)amino, prop-2-en-1-ylamino, diprop-2-en-1-ylamino, bis(2-methylprop-2-en-1-yl)amino, prop-2-yn-1-ylamino, bis(prop-2-yn-1-yl)amino, (pyrazin-2-ylmethyl)amino, (6-methylpyridin-2-ylmethyl)amino, bis(6-methyl-pyridin-2-ylmethyl)amino or (pyridin-2-ylmethyl)amino;

In a fourth embodiment of the present invention,
(a) preferred compounds of the formula (I) are those in which the $R^3$ and $R^4$ radicals are each independently hydrogen, halogen, alkyl, cycloalkyl, haloalkyl, cyano and/or hydroxyl;
(b) further preferred compounds of the formula (I) are those in which the $R^3$ and $R^4$ radicals are each independently hydrogen, halogen and/or alkyl;
(c) especially preferred compounds of the formula (I) are those in which the $R^3$ and $R^4$ radicals are each independently hydrogen, chlorine and/or methyl;

In a fifth embodiment of the present invention,
(a) preferred compounds of the formula (I) are those in which the $R^5$ radical is halogen, alkyl, haloalkyl, alkoxy, haloalkoxy, alkylsulphanyl, alkylsulphinyl, haloalkylsulphinyl, alkylsulphonyl, cyano, dialkylamino or heteroaryl, where the heteroaromatic ring may optionally be mono- or polysubstituted by one or more substituents selected independently from halogen, alkyl, haloalkyl and alkoxy;
(b) more preferred compounds of the formula (I) are those in which the $R^5$ radical is halogen, alkyl, haloalkyl, alkoxy, haloalkoxy, alkylsulphanyl, alkylsulphinyl, haloalkylsulphinyl, alkylsulphonyl, cyano, dialkylamino or heteroaryl, where the heteroaromatic ring may optionally be mono- or polysubstituted by one or more substituents selected independently from halogen and alkyl; and
(c) especially preferred compounds of the formula (I) are those in which the $R^5$ radical is chlorine, bromine, methyl, $CF_3$, methoxy, ethoxy, propoxy, propan-2-yloxy, dimethylamino, cyano, methylsulphanyl, methylsulphinyl, methylsulphonyl, 1H-pyrazol-1-yl, 1H-imidazol-1-yl or 4-fluoro-1H-pyrazol-1-yl.

In a further embodiment of the present invention, preferred compounds of the general formula (I) are those in which
the X radical is phenyl, 2-pyridyl or 3-pyridyl, each of which is substituted by one or more substituents selected from the group consisting of halogen, alkyl, haloalkyl, alkoxy, haloalkoxy, alkylsulphanyl, haloalkylsulphanyl, alkylsulphinyl, haloalkylsulphinyl, alkylsulphonyl, haloalkylsulphonyl, cyano, nitro and dialkylamino; or phenyl, 2-pyridyl and 3-pyridyl optionally substituted by one or more halogen atoms, cyano, nitro, alkyl, alkoxy or haloalkyl, where vicinal alkyl, haloalkyl and/or alkoxy groups on the phenyl substituent, 2-pyridyl substituent or 3-pyridyl substituent, together with the carbon atoms to which they are bonded, may form a five- to seven-membered cyclic system which contains 0 to 2 oxygen or nitrogen atoms, where no two oxygen atoms are directly bonded to one another, and the alkyl moiety thereof may optionally be substituted by one or more halogen atoms and/or further alkyl radicals;
the $R^1$ radical is hydrogen, alkyl which is optionally mono- or independently polysubstituted by alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl and/or cycloalkyl;
alkenyl which is optionally mono- or independently polysubstituted by halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl and/or cycloalkyl;
cycloalkyl which is optionally mono- or independently polysubstituted by alkyl, haloalkyl and/or halogen;
haloalkyl which is optionally mono- or independently polysubstituted by alkoxy, alkylsulphanyl, haloalkylsulphanyl, alkylsulphinyl, haloalkylsulphinyl, alkylsulphonyl, haloalkylsulphonyl and/or phenyl;
CH=NOH, CH=NOCH$_3$ or CN;
the $R^2$ radical is amino and substituted amino, where the substituted amino may be mono- or independently disubstituted by alkyl, haloalkyl, cycloalkylalkyl, optionally halogen- or phenyl-substituted alkenyl, alkynyl, heterocyclylalkyl and/or heteroarylalkyl, where the heteroaromatic ring may optionally be mono- or polysubstituted by one or more substituents selected independently from halogen, alkyl, haloalkyl and alkoxy; benzyl, where the phenyl ring in the benzyl may optionally be mono- or polysubstituted by one or more substituents selected independently from halogen, alkyl, haloalkyl and alkoxy;
the $R^3$ and $R^4$ radicals are each independently hydrogen, halogen, alkyl, cycloalkyl, haloalkyl, cyano and/or hydroxyl and
the $R^5$ radical is halogen, alkyl, haloalkyl, hydroxyl, alkoxy, haloalkoxy, alkylsulphanyl, haloalkylsulphanyl, alkylsulphinyl, haloalkylsulphinyl, alkylsulphonyl, haloalkylsulphonyl, cyano, amino, alkylamino, dialkylamino, alkylsulphonylamino, dialkylsulphonylamino or heteroaryl, where the heteroaromatic ring may optionally be mono- or polysubstituted by one or more substituents selected independently from halogen, alkyl, haloalkyl and alkoxy.

In a further embodiment of the present invention, especially preferred compounds of the general formula (I) are those in which
the X radical is phenyl, 2-pyridyl or 3-pyridyl, each of which is substituted by one or more substituents selected from the group consisting of fluorine, chlorine, bromine, iodine, $CF_3$, methoxy, ethoxy, propanyloxy, trifluoroethoxy, methylsulphanyl, 2,2,2-trifluoroethylsulphanyl, methylsulphinyl, 2,2,2-trifluoroethylsulphinyl, methylsulphonyl, 2,2,2-trifluoroethylsulphonyl, cyano and dimethylamino; or phenyl optionally substituted by one or more halogen atoms, cyano, nitro, methyl, methoxy or $CF_3$, where vicinal alkyl or alkoxy groups on the phenyl substituent, together with the carbon atoms to which they are bonded, may form a five- to seven-membered cyclic system which contains 1 or 2 oxygen atoms, where no two oxygen atoms are directly bonded to one another, and the alkyl moiety thereof may be substituted by one or more further alkyl radicals;
the $R^1$ radical is $CH_3$, $CH_2CH_3$, $CH(CH_3)_2$, $CH_2CH_3CH_3$, $C(CH_3)_3$, $C(OCH_3)HCH_2CH_3$, $CH(OCH_3)_2$, $CH=CH_2$, prop-1-en-2-yl, cyclopropyl, $CF_3$, $CHFCH_3$, $CHF_2$, $CF_2Cl$, $CF_2Br$, $CF_2CF_3$, $CF_2CH_3$, $CF_2CF_2CF_3$, $CF_2CF_2H$, 2-fluoropropan-2-yl, 1,1,2,2-tetrafluoro-2-methoxyethyl, CH=NOH, CH=NOCH$_3$ or CN,
the $R^2$ radical is amino, methylamino, dimethylamino, benzylamino, dibenzylamino, (4-chlorobenzyl)amino, bis(4-chlorobenzyl)amino, (4-methoxybenzyl)amino, bis(4-methoxybenzyl)amino, (2-methylprop-2-en-1-yl)amino, prop-2-en-1-ylamino, diprop-2-en-1-ylamino, bis(2-methylprop-2-en-1-yl)amino, prop-2-yn-1-ylamino, bis(prop-2-yn-1-yl)amino, (pyrazin-2-ylmethyl)amino, (6-methylpyridin-2-ylmethyl)amino, bis(6-methyl-pyridin-2-ylmethyl)amino or (pyridin-2-ylmethyl)amino;
the $R^3$ and $R^4$ radicals are each independently hydrogen, chlorine and/or methyl and
the $R^5$ radical is chlorine, bromine, methyl, $CF_3$, methoxy, ethoxy, propoxy, propan-2-yloxy, dimethylamino, cyano, methylsulphanyl, methylsulphinyl, methylsulphonyl, 1H-pyrazol-1-yl, 1H-imidazol-1-yl or 4-fluoro-1H-pyrazol-1-yl.

In a further embodiment of the present invention, especially preferred compounds of the general formula (I) are those in which
the X radical is phenyl, 2-pyridyl or 3-pyridyl, each of which is substituted by one or more substituents selected from the group consisting of fluorine, chlorine, bromine, iodine, $CF_3$, methoxy, ethoxy, propanyloxy, trifluoroethoxy, methylsulphanyl, 2,2,2-trifluoroethylsulphanyl, 2,2,2-trifluoroethylsulphinyl, cyano and dimethylamino; or phenyl optionally substituted by one or more halogen atoms, cyano or $CF_3$, where vicinal alkyl or alkoxy groups on the phenyl substituent, together with the carbon atoms to which they are bonded, may form a five- to seven-membered cyclic system which contains 1 or 2 oxygen atoms, where no two oxygen atoms are directly bonded to one another, and the alkyl moiety thereof may be substituted by one or more further alkyl radicals;

the $R^1$ radical is $CH_3$, $CH_2CH_3$, $CH(CH_3)_2$, $CH_2CH_3CH_3$, $C(CH_3)_3$, $C(OCH_3)HCH_2CH_3$, $CH(OCH_3)_2$, $CH=CH_2$, prop-1-en-2-yl, cyclopropyl, $CF_3$, $CHFCH_3$, $CHF_2$, $CF_2Cl$, $CF_2CF_3$, $CF_2CH_3$, $CF_2CF_2CF_3$, $CF_2CF_2H$, 2-fluoropropan-2-yl, 1,1,2,2-tetrafluoro-2-methoxyethyl, $CH=NOH$, $CH=NOCH_3$ or CN, the $R^2$ radical is amino, methylamino, dimethylamino, benzylamino, dibenzylamino, (4-chlorobenzyl)amino, bis(4-chlorobenzyl)amino, (4-methoxybenzyl)amino, bis(4-methoxybenzyl)amino, (2-methylprop-2-en-1-yl)amino, prop-2-en-1-ylamino, diprop-2-en-1-ylamino, bis(2-methylprop-2-en-1-yl)amino, bis(prop-2-yn-1-yl)amino, (pyrazin-2-ylmethyl)amino, bis(6-methyl-pyridin-2-ylmethyl)amino or (pyridin-2-ylmethyl)amino;

the $R^3$ and $R^4$ radicals are each independently hydrogen, chlorine and/or methyl and the $R^5$ radical is chlorine, bromine, methyl, $CF_3$, methoxy, ethoxy, propoxy, propan-2-yloxy, dimethylamino, cyano, methylsulphanyl, methylsulphinyl, methylsulphonyl, 1H-pyrazol-1-yl, 1H-imidazol-1-yl or 4-fluoro-1H-pyrazol-1-yl.

In a further embodiment of the present invention, especially preferred compounds of the general formula (I) are those in which the X radical is phenyl or 2-pyridyl, each of which is substituted by one or more substituents selected from the group consisting of fluorine, chlorine, bromine, iodine, $CF_3$, methoxy, ethoxy, propanyloxy, trifluoroethoxy, cyano and dimethylamino; or phenyl optionally substituted by one or more halogen atoms, cyano or $CF_3$, where vicinal alkyl or alkoxy groups on the phenyl substituent, together with the carbon atoms to which they are bonded, may form a five- to seven-membered cyclic system which contains 1 or 2 oxygen atoms, where no two oxygen atoms are directly bonded to one another, and the alkyl moiety thereof may be substituted by one or more further alkyl radicals;

the $R^1$ radical is $CH_2CH_3$, $CH(CH_3)_2$, $CH_2CH_3CH_3$, $C(OCH_3)HCH_2CH_3$, $CH=CH_2$, prop-1-en-2-yl, cyclopropyl, $CF_3$, $CHF_2$, $CF_2Cl$, $CF_2CF_3$, $CF_2CH_3$, $CF_2CF_2CF_3$, $CF_2CF_2H$, 2-fluoropropan-2-yl or 1,1,2,2-tetrafluoro-2-methoxyethyl, the $R^2$ radical is amino, dimethylamino, benzylamino, (4-methoxybenzyl)amino, bis(4-methoxybenzyl)amino, (2-methylprop-2-en-1-yl)amino or diprop-2-en-1-ylamino, the $R^3$ and $R^4$ radicals are each hydrogen stehen the $R^5$ radical is methyl, $CF_3$, methoxy, ethoxy, propoxy, propan-2-yloxy, cyano, methylsulphanyl or 1H-imidazol-1-yl.

In the context of the present invention, the compound of the formula (I) also includes compounds quaternized at a nitrogen atom by a) protonation, b) alkylation or c) oxidation.

The compounds of the formula (I) may form salts as a result of addition of a suitable inorganic or organic acid, for example HCl, HBr, $H_2SO_4$ or $HNO_3$, or else oxalic acid or sulphonic acids, onto a basic group, for example amino or alkylamino. Suitable substituents present in deprotonated form, for example sulphonic acids or carboxylic acids, can form internal salts with groups which are themselves protonatable, such as amino groups. Salts can likewise be formed by replacing the hydrogen in suitable substituents, for example sulphonic acids or carboxylic acids, with a cation suitable in the agrochemical sector. These salts are, for example, metal salts, especially alkali metal salts or alkaline earth metal salts, especially sodium salts and potassium salts, or else ammonium salts, salts with organic amines or quaternary ammonium salts having cations of the formula [NRR'R''R''']$^+$ in which R to R''' are each independently an organic radical, especially alkyl, aryl, aralkyl or alkylaryl.

In the formula (I) and all other formulae in the present invention, the alkyl, alkoxy, haloalkyl, haloalkoxy, alkylamino, alkylsulphinyl and alkylsulphonyl radicals and the corresponding unsaturated and/or substituted radicals may each be straight-chain or branched in the carbon skeleton. Unless stated specifically, the lower carbon skeletons are preferred for these radicals, for example having 1 to 6 carbon atoms, especially 1 to 4 carbon atoms, or in the case of unsaturated groups having 2 to 6 carbon atoms, especially 2 to 4 carbon atoms. Alkyl radicals, including in the combined definitions such as alkoxy, haloalkyl, etc., are, for example, methyl; ethyl; propyl such as n- or i-propyl; butyl such as n-, t- or 2-butyl; pentyl such as n-pentyl, isopentyl and neopentyl; hexyl such as n-hexyl, i-hexyl, 3-methylpentyl, 2,2-dimethylbutyl and 2,3-dimethylbutyl; and heptyl such as n-heptyl, 1-methylhexyl and 1,4-dimethylpentyl; alkenyl and alkynyl radicals are defined as the possible unsaturated radicals corresponding to the alkyl radicals; where at least one double bond or triple bond, preferably one double bond or triple bond, is present. Alkenyl is, for example, vinyl, 1-allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl/propynyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups may be in bi- or tricyclic form.

When haloalkyl groups and haloalkyl radicals of haloalkoxy, haloalkenyl, haloalkynyl inter alia are specified, the lower carbon skeletons are preferred for these radicals, for example having 1 to 6 carbon atoms or 2 to 6, especially 1 to 4, carbon atoms or preferably 2 to 4 carbon atoms, and the corresponding unsaturated and/or substituted radicals are each straight-chain or branched in the carbon skeleton. Examples are trifluoromethyl, difluoromethyl, 2,2,2-trifluoroethyl, trifluoroallyl, 1-chloroprop-1-yl-3-yl.

Alkylene groups in these radicals are the lower carbon skeletons, for example those having 1 to 10 carbon atoms, especially 1 to 6 carbon atoms or preferably 2 to 4 carbon atoms, and the corresponding unsaturated and/or substituted radicals in the carbon skeleton, which may each be straight-chain or branched. Examples are methylene, ethylene, n- and isopropylene and n-, s-, t-butylene.

Hydroxyalkyl groups in these radicals are the lower carbon skeletons, for example those having 1 to 6 carbon atoms, especially 1 to 4 carbon atoms, and the corresponding unsaturated and/or substituted radicals in the carbon skeleton, which may each be straight-chain or branched. Examples thereof are 1,2-dihydroxyethyl and 3-hydroxypropyl.

Halogen is fluorine, chlorine, bromine or iodine; haloalkyl, haloalkenyl and haloalkynyl are, respectively, alkyl, alkenyl and alkynyl which are partly or fully substituted by halogen, preferably by fluorine, chlorine or bromine, especially by fluorine and/or chlorine, examples being monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$, and $OCH_2CH_2Cl$; this correspondingly applies to haloalkenyl and other halogen-substituted radicals.

Aryl is a monocyclic, bicyclic or polycyclic aromatic system, for example phenyl or naphthyl, preferably phenyl.

A heterocyclic radical (heterocyclyl) contains at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the bonding site is localized on one ring atom.

When the heterocyclyl radical or the heterocyclic ring is optionally substituted, it may be fused to other carbocyclic or heterocyclic rings. In the case of optionally substituted heterocyclyl, polycyclic systems are also included, for example 8-azabicyclo[3.2.1]octanyl or 1-azabicyclo[2.2.1]heptyl. In the case of optionally substituted heterocyclyl, spirocyclic systems are also included, for example 1-oxa-5-azaspiro[2.3]hexyl.

Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent.

The term "heteroaryl" in the context of the present invention is understood to mean systems as defined above under "heterocyclyl", but which are heteroaromatic, i.e. are a fully unsaturated, aromatic heterocyclic compound.

The definition "substituted by one or more radicals", unless defined differently, independently means one or more identical or different radicals, where two or more radicals on one cycle as a base skeleton may form one or more rings.

Substituted radicals such as a substituted alkyl, alkenyl, alkynyl, cycloalkyl, cycloalkenyl, aryl, phenyl, benzyl, heterocyclyl and heteroaryl radicals are, for example, a substituted radical derived from the unsubstituted base skeleton, where the substituents are, for example, one or more, preferably 1, 2 or 3, radicals from the group of halogen, alkoxy, alkylthio, hydroxyl, amino, nitro, carboxyl or a group equivalent to the carboxyl group, cyano, isocyano, azido, alkoxycarbonyl, alkylcarbonyl, formyl, carbamoyl, mono- and dialkylaminocarbonyl, substituted amino such as acylamino, mono- and dialkylamino, trialkylsilyl and optionally substituted cycloalkyl, optionally substituted aryl, optionally substituted heterocyclyl, where each of the latter cyclic groups may also be bonded via heteroatoms or divalent functional groups as for the alkyl radicals mentioned, and alkylsulphinyl, including both enantiomers of the alkylsulphonyl group, alkylsulphonyl, alkylphosphinyl, alkylphosphonyl and, in the case of cyclic radicals (="cyclic base skeleton"), also alkyl, haloalkyl, alkylthioalkyl, alkoxyalkyl, optionally substituted mono- and dialkylaminoalkyl and hydroxyalkyl; the term "substituted radicals", such as substituted alkyl, etc. includes, as substituents, in addition to the saturated hydrocarbonaceous radicals mentioned, corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, optionally substituted cycloalkenyl, optionally substituted cycloalkynyl, phenyl, phenoxy. etc. In the case of substituted cyclic radicals with aliphatic moieties in the ring, also included are cyclic systems with those substituents which are bonded to the ring by a double bond, for example with an alkylidene group such as methylidene or ethylidene or an oxo group, imino group or substituted imino group.

When two or more radicals form one or more rings, these may be carbocyclic, heterocyclic, saturated, partly saturated, unsaturated, for example also aromatic and optionally further substituted. The fused rings are preferably 5- or 6-membered rings, particular preference being given to benzofused cycles.

The substituents mentioned by way of example ("first substituent level") may, if they contain hydrocarboneous moieties, optionally be further substituted therein ("second substituent level"), for example by one of the substituents as defined for the first substituent level. Corresponding further substituent levels are possible. The term "substituted radical" preferably encompasses just one or two substituent levels.

Preferred substituents for the substituent levels are, for example, amino, hydroxyl, halogen, nitro, cyano, isocyano, mercapto, isothiocyanato, carboxyl, carbonamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphenyl, alkylsulphinyl, including both enantiomers of the alkylsulphinyl group, alkylsulphonyl, monoalkylaminosulphonyl, dialkylaminosulphonyl, alkylphosphinyl, alkylphosphonyl, including both enantiomers for alkylphosphinyl and alkylphosphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

As already mentioned, in the case of radicals with carbon atoms, preference is given to those having 1 to 6 carbon atoms, preferably 1 to 4 carbon atoms, especially 1 or 2 carbon atoms. Preference is generally given to substituents from the group of halogen, for example fluorine, chlorine and bromine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano.

Optionally substituted aryl or heteroaryl is preferably phenyl or heteroaryl which is unsubstituted or mono- or polysubstituted, preferably up to trisubstituted, by identical of different radicals from the group of halogen, $(C_1-C_4)$-alkyl, $(C_3-C_6)$-cycloalkyl, $(C_1-C_4)$-alkoxy, $(C_1-C_4)$-haloalkyl, $(C_1-C_4)$-haloalkoxy, $(C_1-C_4)$-alkylthio, cyano and nitro, for example o-, m- and p-tolyl, dimethylphenyls, 2-, 3- and 4-chlorophenyl, 2-, 3- and 4-trifluoromethyl and 2-, 3- and 4-trichloromethylphenyl, 2,4-, 3,5-, 2,5- and 2,3-dichlorophenyl, o-, m- and p-methoxyphenyl.

The inventive compounds may be present as mixtures of different possible isomeric forms, especially of stereoisomers, for example, E and Z isomers, threo and erythro isomers, and optical isomers, but if appropriate also of tautomers. Both the E and Z isomers, and the threo and erythro isomers, and the optical isomers, any desired mixtures of these isomers, and the possible tautomeric forms are claimed.

The inventive compounds of the general formula (I) are obtainable by various preparation processes, which likewise form part of the subject-matter of the present invention. To differentiate the individual preparation processes, the compounds of the general formula (I) are divided into the compounds of the general formulae (IA), (IB) and (IC).

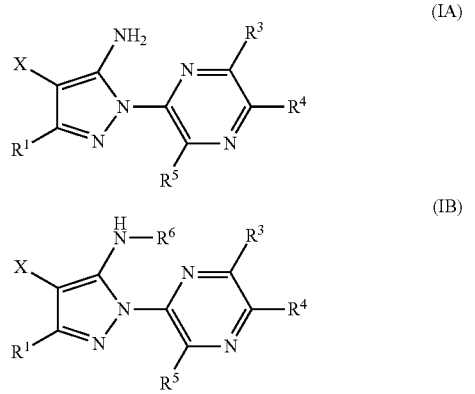

(IA)

(IB)

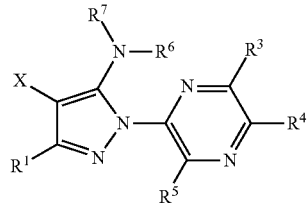

(IC)

where

X, $R^1$, $R^3$, $R^4$ and $R^5$ are each as defined above and $R^6$, $R^7$ is alkyl, haloalkyl, alkoxyalkyl, alkylsulphanylalkyl, alkylsulphinylalkyl, alkylsulphonylalkyl, alkylcarbonyl, cycloalkyl, cycloalkylalkyl, alkenyl (optionally substituted by halogen, cyano, alkoxy, alkoxycarbonyl and phenyl, where the phenyl ring is optionally mono- or polysubstituted by one or more substituents selected independently from halogen, alkyl, haloalkyl and alkoxy), alkynyl, alkoxycarbonyl, alkenyloxycarbonyl, alkynyloxycarbonyl, alkoxycarbonylalkyl, alkoxycarbonylcarbonyl, heterocyclylalkyl, heteroarylalkyl (where the heteroaromatic ring may optionally be mono- or polysubstituted by one or more substituents selected independently from halogen, alkyl, haloalkyl and alkoxy), benzyl or phenylcarbonyl (where the phenyl ring in the benzyl and phenylcarbonyl is optionally mono- or polysubstituted by one or more substituents selected independently from halogen, alkyl, haloalkyl and alkoxy).

Process (A)

Compounds of the formula (IA) are synthesized, for example, by the process (A) which follows:

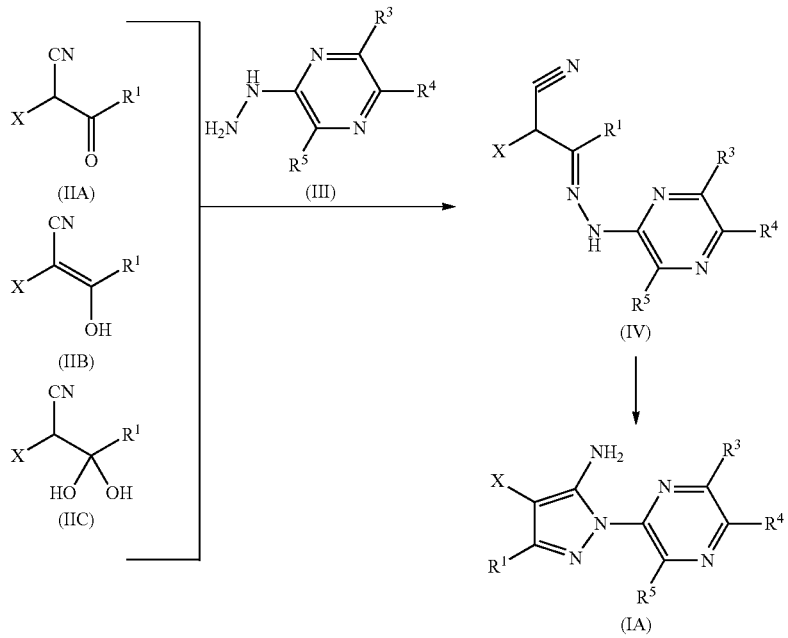

where X, $R^1$, $R^3$, $R^4$ and $R^5$ are each as defined above.

In the process (A) according to the invention for preparing the compounds of the formula (IA), keto nitriles or the tautomers or hydrates thereof, of the formulae (IIA), (IIB) and (IIC), are condensed with pyrazinylhydrazines of the general formula (III), which first forms hydrazones of the formula (IV) as an intermediate and, in the course of a prolonged reaction time and at relatively higher temperature, the ring closure proceeds to give the aminopyrazole of the formula (IA). It is possible to add acids as a catalyst, in which case inorganic acids such as hydrochloric acid and organic acids such as sulphonic acids or acetic acid may be suitable.

The synthesis of structurally related aminopyrazoles is described in R. Aggarwal et al, Bioorg. Med. Chem. 14 (2006), 6, 1785-1791; S. P. Singh et al, Eur. J. Med. Chem. 40 (2005), 922-927; DE 26 43 640 A; U.S. Pat. No. 3,041,342; WO 2008/077483 A.

The keto nitriles may be present in the tautomeric forms (IIA) and (IIB) and as the hydrate (IIC). The starting compounds may also be used in the form of their salts; for example, the keto nitriles may be used in the form of their alkali metal salts, and the pyrazinylhydrazines in the form of their hydrochlorides.

The keto nitriles of the formula (II) can be prepared by known methods, for example W. R. Nes, Alfred Burger, J. Amer. Chem. Soc. 72 (1950), 5409-5413.

Some of the pyrazinylhydrazines of the formula (III) are commercially available. Pyrazinylhydrazines of the formula (III) are prepared, for example, by the methods described in Methoden der Organischen Chemie [Methods of Organic Chemistry] (Houben-Weyl), Organische Stickstoff-Verbindungen [Organic Nitrogen Compounds], volume E 16a, part 1, p. 678-775, Georg Thieme Verlag Stuttgart- New York, 1990 and WO 98/32739 A.

Process (B)

Alternatively, compounds of the formula (IA) can be synthesized by process (B) according to the invention:

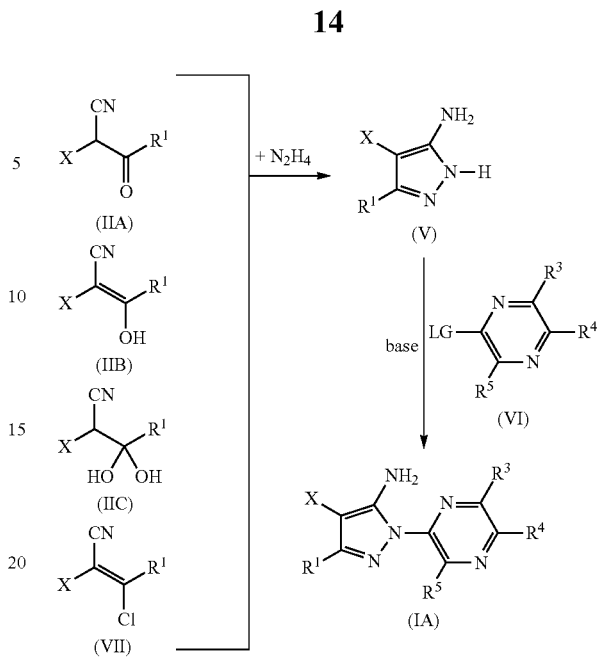

LG=halogen or alkylsulphonyl
where X, $R^1$, $R^3$, $R^4$ and $R^5$ are each as defined above.

In the process (B) according to the invention for preparing the compounds of the formula (IA), 1H-aminopyrazoles of the formula (V) are reacted with pyrazinyl halides or pyrazinyl alkyl sulphones of the formula (VI) in the presence of a base in organic solvents, preferably forming a particular isomer, the aminopyrazole of the formula (IA).

The 1H-aminopyrazoles of the formula (V) can be prepared by known methods (see also DE-A 2643640, C. Chen et al, Bioorg. Med. Chem. Lett., 14 (2004), 14, 3669; Gilligan, Paul J. et al, Bioorg. Med. Chem., 8, (2000), 1, 181-190).

Some of the pyrazinyl halides or pyrazinyl alkyl sulphones of the formula (VI) are commercially available or can be synthesized by methods known to those skilled in the art. Reactions of pyrazinyl halides with 1H-pyrazoles are described, inter alia, in: Journal of Chemical Research, Synopses, 1989 (7), 189 and Dalton Transactions, 2003 (10), 2053-2060.

Process (C)

Compounds of the formula (IA) can alternatively be synthesized, for example, by the process (C) which follows:

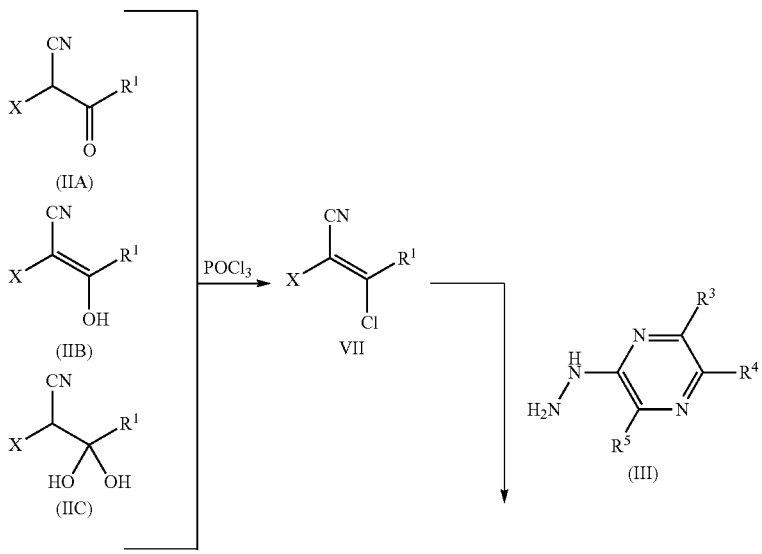

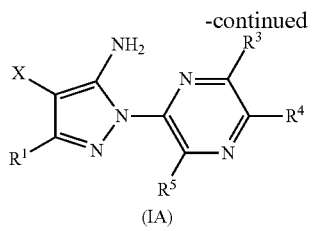

(IA)

where X, $R^1$, $R^3$, $R^4$ and $R^5$ are each as defined above.

In the process (C) according to the invention for preparing the compounds of the formula (IA), keto nitriles or the tautomers or hydrates thereof, of the formulae (IIA), (IIB) and (IIC), are reacted with chlorinating agents, for example phosphoryl chloride, thionyl chloride, phosgene, chlorine or oxalyl chloride, optionally diluted in an inert organic solvent or promoted by auxiliary bases such as nitrogen bases, to give chloroacrylonitriles (VII), the reaction being performable within the temperature range from −20° C. to 120° C.

In a subsequent step, the condensation with pyrazinylhydrazines (III) is effected in a suitable organic solvent in the presence of basic auxiliary reagents, for example alkoxides or nitrogen bases, the reaction being performable within the temperature range from −20° C. to 120° C.

The keto nitriles may be present in the tautomeric forms (IIA) and (IIB) and as the hydrate (IIC). The starting compounds may also be used in the form of their salts; for example, the keto nitriles may be used in the form of their alkali metal salts, and the pyrazinylhydrazines in the form of their hydrochlorides.

The keto nitriles of the formula (II) can—as already mentioned with regard to process (A)—be prepared by known methods: W. R. Nes, Alfred Burger, J. Amer. Chem. Soc. 72 (1950), 5409-5413.

Some of the pyrazinylhydrazines of the formula (III) are commercially available. Pyrazinylhydrazines of the formula (III) are prepared, for example, by the methods described in Methoden der Organischen Chemie (Houben-Weyl), Organische Stickstoff-Verbindungen, volume E 16a, part 1, p. 678-775, Georg Thieme Verlag Stuttgart- New York, 1990 and WO 98/32739 A.

The chloroacrylonitriles of the formula (VII) can likewise be prepared by known methods (see also JP08-208620 (X=4-$CF_3C_6H_6$ and $R^1$=$CF_3$))

Process (D)

Inventive compounds of the formula (IB) and (IC) in which at least one radical of $R^6$ and $R^7$ is not hydrogen (substituted amine) can be synthesized proceeding from the inventive compound (IA) by the process (D) according to the invention:

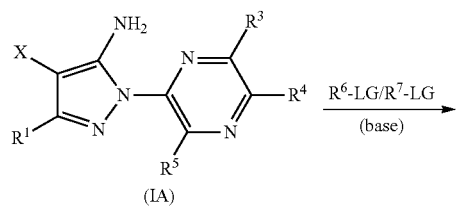

(IA)

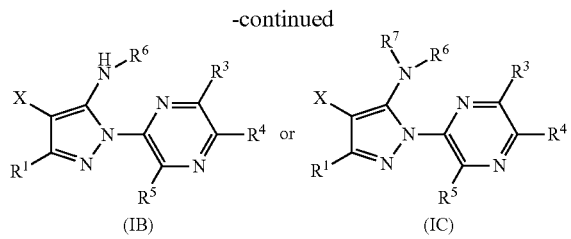

(IB)　　　(IC)

LG=halogen or alkylsulphonyl where X, $R^1$, $R^3$, $R^4$ and $R^5$ are each as defined above;

LG is halogen or alkylsulphonyl; and $R^6$ and $R^7$ are each independently hydrogen, alkyl, haloalkyl, alkoxyalkyl, alkylsulphanylalkyl, alkylsulphinylalkyl, alkylsulphonylalkyl, alkylcarbonyl, cycloalkyl, cycloalkylalkyl, alkenyl, where the above radicals are optionally substituted by halogen, cyano, alkoxy, alkoxycarbonyl and phenyl, where the phenyl ring is optionally mono- or polysubstituted by one or more substituents selected independently from halogen, alkyl, haloalkyl and alkoxy; alkynyl, alkoxycarbonyl, alkenyloxycarbonyl, alkynyloxycarbonyl, alkoxycarbonylalkyl, alkoxycarbonylcarbonyl, heterocyclyl, heteroaryl, heterocyclylalkyl or heteroarylalkyl, where the heterocyclic or heteroaromatic ring may optionally be mono- or polysubstituted by one or more substituents selected independently from halogen, alkyl, haloalkyl and alkoxy; benzyl or phenylcarbonyl, where the phenyl ring in the benzyl and phenylcarbonyl is optionally mono- or polysubstituted by one or more substituents selected independently from halogen, alkyl, haloalkyl and alkoxy; with the proviso that at least one radical of $R^6$ and $R^7$ is not hydrogen.

In the process (D) according to the invention for preparing the compounds of the formula (IB) or (IC), compounds of the formula (IA) are reacted with one or two alkylating agents or acylating agents $R^6$-LG or $R^7$-LG, monosubstitution and disubstitution forming aminopyrazoles of the formulae (IB) and (IC). Suitable alkylating agents are alkyl bromides, alkyl dibromides, alkyl iodides, alkyl diiodides, dialkyl sulphates and alkyl sulphonates. The acylating agents used are carboxylic anhydrides and carbonyl chlorides.

Process (E)

Compounds of the formula (IA) can alternatively be synthesized, for example, by the process (E) which follows:

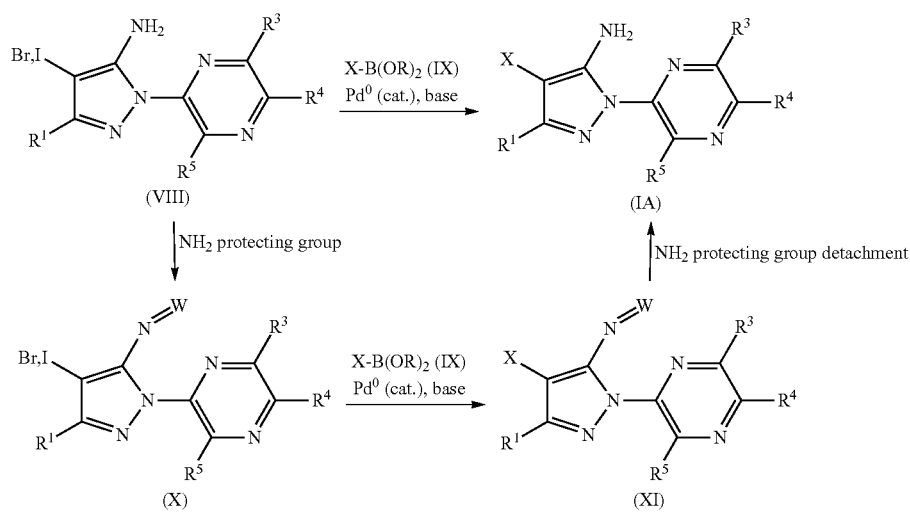

W=protecting group, for example DMF-DMA adduct
where X, $R^1$, $R^3$, $R^4$ and $R^5$ are each as defined above.

In the process (E) according to the invention for preparing the compounds of the formula (IA), bromides or iodides of the formula (VIII) are reacted with boronic acids or boronic esters of the formula (IX) in the presence of suitable palladium catalysts and bases (Suzuki reaction) within the temperature range from −20° C. to 120° C. in suitable solvents.

The bromides or iodides of the formula (VIII) can be prepared by known methods, described, for example, in: Chemistry of Heterocyclic Compounds (New York, N.Y., United States), 41(1), 105-110; 2005; Bioorganic & Medicinal Chemistry, 12, 2004 (12), 3345-3355; Journal of Medicinal Chemistry, 20, 1977 (12), 1562-1569.

Some of the boronic acids or boronic esters of the formula (IX) are commercially available, or they are preparable easily by known methods. This is described, for example, in WO 99/64428 A.

To improve the yields of the Suzuki reaction, the $NH_2$ group of the bromides or iodides of the formula (VIII) can be provided with a protecting group, for example by means of reaction of (VIII) with dimethylformamide dimethyl acetal (DMF-DMA). The resulting imines (XI) can, after successful Suzuki coupling, be converted in the presence of strong acids, for example hydrochloric acid, in suitable solvents, for example methanol, to the end compounds (IA).

Examples of reactions of aminopyrazoles with DMF-DMA are described, for example, in US 2006/0014802 A, Bioorganic & Medicinal Chemistry Letters, 18, 2008 (3), 959-962.

The inventive compounds of the general formula (I), given good plant tolerance, favourable toxicity to warm-blooded animals and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Anon* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as *Eimeria*.

From the order of the heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare*, *Oniscus asellus* and *Porcellio scaber*.

From the order of the Isoptera, for example, *Reticulitermes* spp. and *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp. and *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni* and *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans* and *Xiphinema* spp.

The inventive compounds can optionally, at certain concentrations or application rates, also be used as herbicides, safeners, growth regulators or agents for improving plant properties, or as microbicides, for example as fungicides, antimycotics, bactericides, viricides (including agents against viroids) or as agents against MLO (mycoplasma-like organisms) and RLO (Rickettsia-like organisms). They can optionally also be used as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers and also microencapsulations in polymeric substances.

These formulations are produced in a known manner, for example by mixing the active ingredients with extenders, i.e. liquid solvents, and/or solid carriers, optionally with the use of surfactants, i.e. emulsifiers and/or dispersants, and/or foam formers. The formulations are produced either in suitable plants or else before or during application.

Suitable substances for use as auxiliaries are those which are suitable for imparting particular properties, such as certain technical properties and/or also particular biological properties, to the composition itself and/or to preparations derived therefrom (for example spray liquors, seed dressings). Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Useful solid carriers include:

for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and their adducts with formaldehyde.

In the formulations it is possible to use tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as low-temperature stabilizers, preservatives, antioxidants, light stabilizers or other agents which improve chemical and/or physical stability.

The formulations contain generally from 0.01 to 98% by weight of active ingredient, preferably from 0.5 to 90%.

The inventive active ingredient may be present in its commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers or semiochemicals.

When used as insecticides, the inventive active ingredients may also be present in their commercially available formulations and in the use forms, prepared from these formulations, as a mixture with synergists. Synergists are compounds which increase the action of the active ingredients, without any need for the synergist added to be active itself.

When used as insecticides, the inventive active ingredients may also be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations may vary within wide limits. The active ingredient concentration of the use forms may be from 0.00000001 to 95% by weight of active ingredient, preferably between 0.00001 and 1% by weight.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which can or cannot be protected by plant variety rights. Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material, and also vegetative and generative propagation material, for example cuttings, tubers, rhizomes, slips and seed.

The inventive treatment of the plants and plant parts with the active ingredients is effected directly or through action on the environment, habitat or storage space thereof by the customary treatment methods, for example by dipping, spraying, evaporation, fogging, scattering, painting on and, in the case of propagation material, especially in the case of seeds, also by applying one or more coats.

As already mentioned above, it is possible in accordance with the invention to treat all plants and parts thereof. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" and "parts of plants" or "plant parts" have been explained above.

More preferably, plants of the plant cultivars which are each commercially available or in use are treated in accordance with the invention. Plant cultivars are understood to mean plants which have new properties ("traits") and have been obtained by conventional breeding, by mutagenesis or by recombinant DNA techniques. They may be cultivars, bio- or genotypes.

Depending on the plant species or plant cultivars, and the location and growth conditions (soils, climate, vegetation period, diet) thereof, the inventive treatment may also result in superadditive ("synergistic") effects. For example, reduced application rates and/or broadening of the activity spectrum and/or an increase in the efficacy of the compounds and compositions used in accordance with the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processibility of the harvested products, which exceed the effects normally to be expected.

The transgenic plants or plant cultivars (i.e. those obtained by genetic engineering) which are treated with preference in accordance with the invention include all plants which, through the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, increased storability and/or processibility of the harvested products. Further and particularly emphasized examples of such properties are a better defence of the plants against animal and microbial pests, such as against insects, mites, phytopathogenic fungi, bacteria and/or viruses, and also increased tolerance of the plants to certain active herbicidal ingredients. Examples of transgenic plants include the important crop plants, such as cereals (wheat, rice), maize, soya, potatoes, sugar beet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are increased defence of the plants against insects, arachnids, nematodes, slugs and snails by toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c Cry2Ab, Cry3Bb and CryIF, and also combinations thereof) (referred to hereinafter as "Bt plants"). Traits that are also particularly emphasized are the increased defence of the plants against fungi, bacteria and viruses by systemic acquired resistance (SAR), systemin, phytoalexins, elicitors and resistance genes, and correspondingly expressed proteins and toxins. Traits that are additionally particularly emphasized are the increased tolerance of the plants to certain active herbicidal ingredients, for example imidazolinones, sulphonylureas, glyphosate or phosphinotricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Boligard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) include the varieties sold under the Clearfield® name (for example maize). Of course, these statements also apply to plant cultivars which have these genetic traits or genetic traits still to be developed and will be developed and/or marketed in the future.

The plants listed can be treated in accordance with the invention particularly advantageously with the compounds of the general formula (I). The preferred ranges stated above for the active ingredients also apply to the treatment of these plants. Particular emphasis is given to the treatment of plants with the compounds or mixtures specifically mentioned in the present text.

In addition, the inventive compounds can be used to control a multitude of different pests, including, for example, harmful sucking insects, biting insects and other pests which are plant parasites, stored material pests, pests which destroy industrial material, and hygiene pests including parasites in the animal health sector, and for the control thereof, for example the elimination and eradication thereof.

The present invention thus also includes a method for controlling pests.

In the animal health sector, i.e. in the field of veterinary medicine, the active ingredients according to the present invention act against animal parasites, especially ectoparasites or endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like, or acaricides such as ticks, for example hard ticks or soft ticks, or mites such as scab mites, harvest mites, bird mites and the like.

These parasites include:

From the order of the Anoplurida, for example, *Haematopinus* spp., *Linognathus* spp., *Pediculus* spp., *Phtirus* spp. and *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus*;

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi*;

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca*;

From the order of the Siphonapterida, for example *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis*;

From the order of the heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp. (e.g. *Supella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*;

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschöngastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi*.

The inventive active ingredients are also suitable for controlling arthropods, helminths and protozoa which attack animals. The animals include agricultural livestock, for example cattle, sheep, goats, horses, pigs, donkeys, camels, buffalo, rabbits, chickens, turkeys, ducks, geese, cultured fish, honeybees. The animals also include domestic animals—also referred to as companion animals—for example dogs, cats, caged birds, aquarium fish, and test animals, for example hamsters, guinea pigs, rats and mice.

The control of these arthropods, helminths and/or protozoa should reduce cases of death and improve the performance (for meat, milk, wool, hides, eggs, honey etc.) and the health of the host animal, and so the use of the inventive active ingredients enables more economically viable and easier animal husbandry.

For example, it is desirable to prevent or to interrupt the uptake of blood from the host by the parasites (if relevant). Control of the parasites can also contribute to preventing the transmission of infectious substances.

The term "control" as used herein with regard to the field of animal health means that the active ingredients act by reducing the occurrence of the parasite in question in an animal infested with such parasites to a harmless level. More specifically, "control" as used herein means that the active ingredient kills the parasite in question, retards its growth or inhibits its proliferation.

In general, the inventive active ingredients can employed directly when they are used for the treatment of animals. They are preferably employed in the form of pharmaceutical compositions which may comprise the pharmaceutically acceptable excipients and/or auxiliaries known in the prior art.

In the sector of animal health and in animal husbandry, the active ingredients are employed in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active ingredient, such as collars, earmarks, tailmarks, limb bands, halters, marking devices, etc. The active ingredients can be formulated as a shampoo or as suitable formulations applicable in aerosols or unpressurized sprays, for example pump sprays and atomizer sprays, In the case of employment for livestock, poultry, domestic pets, etc., the inventive active ingredients can be employed as formulations (for example powders, wettable powders ["WP"], emulsions, emulsifiable concentrates ["EC"], free-flowing compositions, homogeneous solutions and suspension concentrates ["SC"]), which contain the active ingredients in an amount of 1 to 80% by weight, directly or after dilution (e.g. 100- to 10 000-fold dilution), or they can be used as a chemical bath.

In the case of use in the animal health sector, the inventive active ingredients can be used in combination with suitable synergists or other active ingredients, for example acaricides, insecticides, anthelmintics, anti-protozoal agents.

The inventive compounds are especially suitable for use in material protection, preferably for protection of industrial materials, which is understood to mean inanimate materials, such as preferably plastics, adhesives, sizes, papers and cardboards, leather, wood, wood processing products and paints. The compounds according to the invention can at the same time be used for protection of objects which come into contact with saltwater or brackish water, especially of hulls, screens, nets, buildings, moorings and signalling systems, against fouling.

The ready-to-use compositions may optionally comprise further active ingredients for controlling fouling, insects, bacteria or fungi, for example insecticides, herbicides or microbicides (fungicides, antimycotics, bactericides, viricides (including anti-viroidal agents), or anti-MLO (mycoplasma-like organism) and anti-RLO (Rickettsia-like organism) agents.

In addition, the inventive compounds can be used alone or in combinations with other active ingredients as antifouling compositions.

The active ingredients are also suitable for controlling animal pests in the domestic sector, in hygiene and in the protection of stored products, especially insects, arachnids and mites, which are found in enclosed spaces, for example dwellings, factory halls, offices, vehicle cabins and the like. They can be used to control these pests alone or in combination with other active ingredients and auxiliaries in domestic insecticide products. They are active against sensitive and resistant species and against all developmental stages. These pests include:

From the order of the Scorpionidea, for example, *Buthus occitanus*. From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*. From the order of the Araneae, for example, Aviculariidae, Araneidae. From the order of the Opiliones, for example, *Pseudoscorpiones chelifer, Pseudoscorpiones cheiridium, Opiliones phalangium*. From the order of the Isopoda, for example, *Oniscus asellus, Porcellio scaber*. From the order of the Diplopoda, for example, *Blaniulus guttulatus, Polydesmus* spp. From the order of the Chilopoda, for example, *Geophilus* spp. From the order of the Zygentoma, for example, *Ctenolepisma* spp., *Lepisma saccharina, Lepismodes inquilinus*. From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*. From the order of the Saltatoria, for example, *Acheta domesticus*. From the order of the Dermaptera, for example, *Forficula auricularia*. From the order of the Isoptera, for example, *Kalotermes* spp., *Reticulitermes* spp. From the order of the Psocoptera, for example, *Lepinatus* spp., *Liposcelis* spp. From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*. From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*. From the order of the Lepidoptera, for example, *Achroia grisella, Galleria mellonella, Plodia interpunctella, Tinea cloacella, Tinea pellionella, Tineola bisselliella*. From the order of the Siphonaptera, for example, *Ctenocephalides canis, Ctenocephalides felis, Pulex irritans, Tunga penetrans, Xenopsylla cheopis*. From the order of the Hymenoptera, for example, *Camponotus herculeanus, Lasius fuliginosus, Lasius niger, Lasius umbratus, Monomorium pharaonis, Paravespula* spp., *Tetramorium caespitum*. From the order of the Anoplura, for example, *Pediculus humanus capitis, Pediculus humanus corporis, Pemphigus* spp., *Phylloera vastatrix, Phthirus pubis*. From the order of the Heteroptera, for example, *Cimex hemipterus, Cimex lectularius, Rhodinus prolixus, Triatoma infestans*.

In the domestic insecticides sector, they are employed alone or in combination with other suitable active ingredients, such as phosphoric esters, carbamates, pyrethroids, neonicotinoids, growth regulators or active ingredients from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free or passive evaporation systems, moth papers, moth bags and moth gels, as granules or dusts, in baits for spreading or in bait stations.

The present invention is illustrated in more detail by the examples which follow, but they do not restrict the invention in any way.

A. SYNTHESIS EXAMPLES

Preparation of the Compound (26)

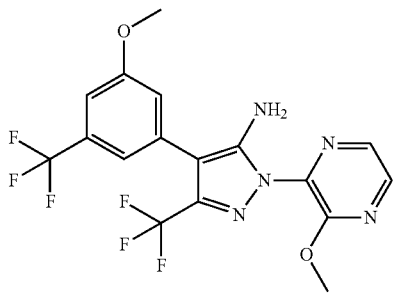 [SMILES: COc1cc(-c2c(C(F)(F)F)nn(-c3nccnc3OC)c2N)cc(C(F)(F)F)c1]

Preparation of the Compounds (107), (108)

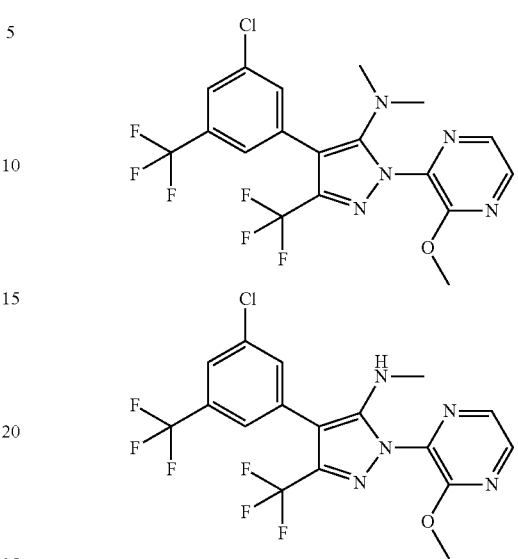

Step 1:

500 mg (1.52 mmol) of 2-[3-methoxy-5-(trifluoromethyl)phenyl]-4,4,4-trifluoro-3-oxobutyronitrile hydrate were initially charged in 1.16 g (7.60 mmol) of phosphoryl chloride and admixed with 0.21 ml (1.52 mmol) of triethylamine. The reaction mixture was stirred at 80-100° C. for 4 h and stirred cautiously into warm water. After extracting with ethyl acetate, the organic phase was dried with magnesium sulphate, filtered and concentrated under reduced pressure. This left 366 mg (73%) of 3-chloro-2-[3-methoxy-5-(trifluoromethyl)phenyl]-4,4,4-trifluorobut-2-enenitrile.

Step 2:

366 mg (1.11 mmol) of 3-chloro-2-[3-methoxy-5-(trifluoromethyl)phenyl]-4,4,4-trifluorobut-2-enenitrile were initially charged in 10 ml of ethanol and admixed with 156 mg (1.11 mmol) of 3-methoxypyrazin-2-ylhydrazine and 0.155 ml (1.11 mmol) of triethylamine. The mixture was heated under reflux for 10 h. After cooling, 75 ml of water were added and the mixture was extracted with ethyl acetate. The organic phase is freed of the solvent and purified by flash chromatography in a cyclohexane/ethyl acetate gradient. This left 180 mg (36%) of 1-(3-methoxypyrazin-2-yl)-4-[3-methoxy-5-(trifluoromethyl)phenyl]-3-(trifluoromethyl)-1H-pyrazol-5-amine.

$^1$H NMR (400 MHz, DMSO-d6), δ 8.44 (d, 1H), 8.25 (d, 1H), 7.21-7.18 (m, 3H), 5.75 (s, 2H, NH$_2$), 4.00 (s, 3H), 3.88 (s, 3H).

150 mg (0.34 mmol) of 1-(3-methoxypyrazin-2-yl)-4-[3-chloro-5-(trifluoromethyl)phenyl]-3-(trifluoromethyl)-1H-pyrazol-5-amine were dissolved in 5 ml of acetonitrile and admixed with 335 mg (1.03 mmol) of caesium carbonate, 4.4 mg (0.02 mmol) of caesium iodide and 97.3 mg (0.67 mmol) of iodomethane. The reaction mixture was stirred at 80° C. for 12 hours, then filtered. The filtrate was chromatographed directly using a silica gel cartridge with a cyclohexane/ethyl acetate gradient. The purified fractions gave the monoalkylated and bisalkylated products.

53% (107) 1-(3-methoxypyrazin-2-yl)-4-[3-chloro-5-(trifluoromethyl)phenyl]-3-(trifluoromethyl)-1H-pyrazole-5-dimethylamine.

$^1$H NMR (400 MHz, DMSO-d6), δ 8.47 (d, 1H), 8.27 (d, 1H), 7.82 (m, 1H), 7.75 (m, 1H), 7.66 (m, 1H), 5.82 (m, 1H), 4.01 (s, 3H), 2.33 (d, 3H).

33% (108) 1-(3-methoxypyrazin-2-yl)-4-[3-chloro-5-(trifluoromethyl)phenyl]-3-(trifluoromethyl)-1H-pyrazole-5-methylamine.

$^1$H NMR (400 MHz, DMSO-d6), δ 8.52 (d, 1H), 8.33 (d, 1H), 7.88 (m, 1H), 7.81 (m, 1H), 7.72 (m, 1H), 4.01 (s, 3H), 2.44 (s, 6H).

Analogous procedures were used to obtain:

TABLE 1

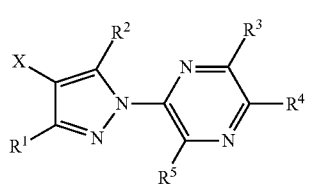

(I)

| Ex. | R$^1$ | R$^2$ | R$^3$ | R$^4$ | R$^5$ | X | log P |
|---|---|---|---|---|---|---|---|
| 1 | CF$_3$ | amino | H | H | chlorine | 3.4-dichlorophenyl | 3.99**; 4.02* |
| 2 | CF$_3$ | amino | H | H | methoxy | 4-bromophenyl | 3.4*** |
| 3 | 1-methoxypropyl | amino | H | H | methoxy | 3.4-dichlorophenyl | |
| 4 | CF$_3$ | amino | H | H | propoxy | 4-bromophenyl | 4.11** |
| 5 | CF$_3$ | amino | H | H | ethoxy | 4-bromophenyl | 3.6** |
| 6 | CF$_3$ | amino | H | H | methoxy | 3.5-dichlorophenyl | 3.95* |

TABLE 1-continued

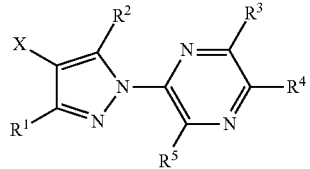
(I)

| Ex. | R¹ | R² | R³ | R⁴ | R⁵ | X | log P |
|---|---|---|---|---|---|---|---|
| 7 | $CF_3$ | amino | H | H | chlorine | 4-chlorophenyl | 3.59* |
| 8 | ethenyl | amino | H | H | methoxy | 3.5-dichlorophenyl | 3.51* |
| 9 | ethenyl | amino | H | H | methoxy | 3-chloro-5-(trifluoromethyl)phenyl | 3.63* |
| 10 | $CF_3$ | amino | H | H | methoxy | 3-chloro-5-(trifluoromethyl)phenyl | 4.07* |
| 11 | chloro(difluoro)methyl | amino | H | H | methoxy | 3,5-bis(trifluoromethyl)phenyl | |
| 12 | $CF_3$ | amino | H | H | ethoxy | 3-chloro-5-(trifluoromethyl)phenyl | 4.47* |
| 13 | $CF_3$ | amino | H | H | propan-2-yloxy | 3-chloro-5-(trifluoromethyl)phenyl | 4.84* |
| 14 | $CF_3$ | amino | H | H | methoxy | 3,5-bis(trifluoromethyl)phenyl | 4.2* |
| 15 | pentafluoroethyl | amino | H | H | methoxy | 3-chloro-5-(trifluoromethyl)phenyl | 4.58* |
| 16 | $CF_3$ | amino | H | H | chlorine | 3-chloro-5-(trifluoromethyl)phenyl | 4.28* |
| 17 | chloro(difluoro)methyl | amino | H | H | methoxy | 3-chloro-5-(trifluoromethyl)phenyl | 4.24* |
| 18 | $CF_3$ | amino | H | H | methoxy | 4-chloro-3-(trifluoromethyl)phenyl | 3.94* |
| 19 | $CF_3$ | amino | chlorine | H | H | 3-chloro-5-(trifluoromethyl)phenyl | 5.26* |
| 20 | 1,1-difluoroethyl | amino | H | H | methoxy | 4-chloro-3-(trifluoromethyl)phenyl | 3.74* |
| 21 | pentafluoroethyl | amino | H | H | methoxy | 3-fluoro-5-(trifluoromethyl)phenyl | 4.23* |
| 22 | $CF_3$ | amino | H | H | methoxy | 3,5-dibromophenyl | 4.1* |
| 23 | $CF_3$ | amino | H | H | $CH_3$ | 3-chloro-5-(trifluoromethyl)phenyl | 4.32* |
| 24 | $CF_3$ | amino | $CH_3$ | H | $CH_3$ | 3-chloro-5-(trifluoromethyl)phenyl | 4.56* |
| 25 | $CF_3$ | amino | H | H | dimethylamino | 3-chloro-5-(trifluoromethyl)phenyl | 4.28* |
| 26 | $CF_3$ | amino | H | H | methoxy | 3-methoxy-5-(trifluoromethyl)phenyl | 3.63* |
| 27 | $CF_3$ | amino | H | H | cyano | 3-chloro-5-(trifluoromethyl)phenyl | 3.93* |
| 28 | $CF_3$ | amino | H | H | methylsulphanyl | 3-chloro-5-(trifluoromethyl)phenyl | 4.9* |
| 29 | $CF_3$ | amino | H | H | methylsulphinyl | 3-chloro-5-(trifluoromethyl)phenyl | 3.29* |
| 30 | $CF_3$ | amino | H | H | methylsulphonyl | 3-chloro-5-(trifluoromethyl)phenyl | 3.54* |
| 31 | $CF_3$ | amino | H | H | 1H-pyrazol-1-yl | 3-chloro-5-(trifluoromethyl)phenyl | 3.94* |
| 32 | $CF_3$ | dibenzylamino | H | H | methoxy | 3-chloro-5-(trifluoromethyl)phenyl | 6.67* |
| 33 | $CF_3$ | benzylamino | H | H | methoxy | 3-chloro-5-(trifluoromethyl)phenyl | 5.28* |
| 34 | $CF_3$ | dibenzylamino | H | H | ethoxy | 3-chloro-5-(trifluoromethyl)phenyl | 7* |
| 35 | $CF_3$ | benzylamino | H | H | ethoxy | 3-chloro-5-(trifluoromethyl)phenyl | 5.62* |
| 36 | $CF_3$ | bis(4-chlorobenzyl)amino | H | H | ethoxy | 3-chloro-5-(trifluoromethyl)phenyl | 7.36** |
| 37 | $CF_3$ | (4-chlorobenzyl)amino | H | H | ethoxy | 3-chloro-5-(trifluoromethyl)phenyl | 5.84* |
| 38 | $CF_3$ | bis(4-chlorobenzyl)amino | H | H | methoxy | 3-chloro-5-(trifluoromethyl)phenyl | 7.11* |
| 39 | $CF_3$ | (4-chlorobenzyl)amino | H | H | methoxy | 3-chloro-5-(trifluoromethyl)phenyl | 5.51* |
| 40 | $CF_3$ | (4-methoxybenzyl)amino | H | H | ethoxy | 3-chloro-5-(trifluoromethyl)phenyl | 5.47* |
| 41 | $CF_3$ | (4-methoxybenzyl)amino | H | H | methoxy | 3-chloro-5-(trifluoromethyl)phenyl | 5.13* |
| 42 | $CF_3$ | bis(4-methoxybenzyl)amino | H | H | methoxy | 3-chloro-5-(trifluoromethyl)phenyl | 6.25* |

TABLE 1-continued

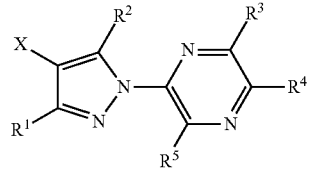

(I)

| Ex. | R$^1$ | R$^2$ | R$^3$ | R$^4$ | R$^5$ | X | log P |
|---|---|---|---|---|---|---|---|
| 43 | CF$_3$ | bis(4-methoxybenzyl)amino | H | H | ethoxy | 3-chloro-5-(trifluoromethyl)phenyl | 6.57* |
| 44 | CF$_3$ | amino | H | H | 1H-imidazol-1-yl | 3-chloro-5-(trifluoromethyl)phenyl | 2.76* |
| 45 | CF$_3$ | amino | H | H | 4-fluoro-1H-pyrazol-1-yl | 3-chloro-5-(trifluoromethyl)phenyl | 4.24* |
| 46 | heptafluoropropyl | amino | H | H | methoxy | 3-chloro-5-(trifluoromethyl)phenyl | 4.91* |
| 47 | 1,1,2,2-tetrafluoro-2-methoxyethyl | amino | H | H | methoxy | 3-chloro-5-(trifluoromethyl)phenyl | 3.98* |
| 48 | CF$_3$ | amino | H | H | methoxy | 7-chloro-1,3-benzodioxol-5-yl | 3.14* |
| 49 | CF$_3$ | amino | H | H | methoxy | pyridin-2-yl | 2.59* |
| 50 | CF$_3$ | amino | H | H | methoxy | 5-bromopyridin-3-yl | 2.62* |
| 51 | pentafluoroethyl | amino | H | H | methoxy | 3-chloro-4,5-dimethoxyphenyl | 3.8* |
| 52 | CF$_3$ | amino | H | H | methoxy | 3,5-dichloropyridin-2-yl | 2.94* |
| 53 | CF$_3$ | amino | H | H | methoxy | 5-chloropyridin-2-yl | 3.55* |
| 54 | pentafluoroethyl | amino | H | H | methoxy | 5-chloropyridin-2-yl | 4.17* |
| 55 | CF$_3$ | amino | H | H | methoxy | 6-chloro-4-(trifluoromethyl)pyridin-2-yl | 4.54* |
| 56 | CF$_3$ | amino | H | H | chlorine | 3,5-dichlorophenyl | 4.16* |
| 57 | CF$_3$ | amino | H | H | methoxy | 2-chloropyridin-3-yl | 2.19* |
| 58 | pentafluoroethyl | amino | H | H | methoxy | 6-chloropyridin-3-yl | 3.14* |
| 59 | 1,1,2,2-tetrafluoroethyl | amino | H | H | methoxy | 3-chloro-5-(trifluoromethyl)phenyl | 4.05* |
| 60 | 1,1,2,2-tetrafluoroethyl | amino | H | H | ethoxy | 3-chloro-5-(trifluoromethyl)phenyl | |
| 61 | 1,1,2,2-tetrafluoroethyl | (pyrazin-2-ylmethyl)amino | H | H | methoxy | 3-chloro-5-(trifluoromethyl)phenyl | |
| 62 | 1,1,2,2-tetrafluoroethyl | (2-methylprop-2-en-1-yl)amino | H | H | methoxy | 3-chloro-5-(trifluoromethyl)phenyl | |
| 63 | 1,1,2,2-tetrafluoroethyl | prop-2-en-1-ylamino | H | H | methoxy | 3-chloro-5-(trifluoromethyl)phenyl | |
| 64 | 1,1,2,2-tetrafluoroethyl | (pyridin-2-ylmethyl)amino | H | H | methoxy | 3-chloro-5-(trifluoromethyl)phenyl | |
| 65 | 1,1,2,2-tetrafluoroethyl | amino | H | H | methoxy | 7-chloro-1,3-benzodioxol-5-yl | 3.18* |
| 66 | 1,1,2,2-tetrafluoroethyl | amino | H | H | methoxy | 7-chloro-2,3-dihydro-1-benzofur-5-yl | 3.22* |
| 67 | 1,1,2,2-tetrafluoroethyl | amino | H | H | methoxy | 7-(trifluoromethyl)-1,3-benzodioxol-5-yl | |
| 68 | 1,1,2,2-tetrafluoroethyl | amino | H | H | methoxy | 7-bromo-1,3-benzodioxol-5-yl | |
| 69 | pentafluoroethyl | amino | H | H | methoxy | 7-chloro-2,3-dihydro-1-benzofur-5-yl | |
| 70 | pentafluoroethyl | amino | H | H | methoxy | 7-(trifluoromethyl)-1,3-benzodioxol-5-yl | |
| 71 | pentafluoroethyl | amino | H | H | methoxy | 7-bromo-1,3-benzodioxol-5-yl | |
| 72 | CF$_3$. | amino | H | H | methoxy | 7-chloro-2,3-dihydro-1-benzofur-5-yl | |
| 73 | CF$_3$ | amino | H | H | methoxy | 7-(trifluoromethyl)-1,3-benzodioxol-5-yl | |
| 74 | CF$_3$ | amino | H | H | methoxy | 7-bromo-1,3-benzodioxol-5-yl | 3.18* |
| 75 | CH$_3$ | amino | H | H | methoxy | 7-chloro-1,3-benzodioxol-5-yl | 2.26* |
| 76 | ethyl | amino | H | H | ethoxy | 7-chloro-1,3-benzodioxol-5-yl | 2.57* |
| 77 | propan-2-yl | amino | H | H | methoxy | 7-chloro-1,3-benzodioxol-5-yl | 2.96* |
| 78 | tert-butyl | amino | H | H | methoxy | 7-chloro-1,3-benzodioxol-5-yl | |
| 79 | cyclopropyl | amino | H | H | methoxy | 7-chloro-1,3-benzodioxol-5-yl | 2.79* |
| 80 | CH$_3$ | amino | H | H | methoxy | 7-chloro-2,3-dihydro-1-benzofur-5-yl | |
| 81 | ethyl | amino | H | H | methoxy | 7-chloro-2,3-dihydro-1-benzofur-5-yl | |
| 82 | propan-2-yl | amino | H | H | methoxy | 7-chloro-2,3-dihydro-1-benzofur-5-yl | |
| 83 | tert-butyl | amino | H | H | methoxy | 7-chloro-2,3-dihydro-1-benzofur-5-yl | |
| 84 | cyclopropyl | amino | H | H | methoxy | 7-chloro-2,3-dihydro-1-benzofur-5-yl | |

TABLE 1-continued (I)

| Ex. | R¹ | R² | R³ | R⁴ | R⁵ | X | log P |
|---|---|---|---|---|---|---|---|
| 85 | tert-butyl | amino | H | H | methoxy | 3-chloro-5-(trifluoromethyl)phenyl | |
| 86 | CF₃ | amino | H | H | methoxy | 3,4-dichloro-5-(trifluoromethyl)phenyl | 4.47** |
| 87 | CF₃ | amino | H | H | methoxy | 3,4,5-trichlorophenyl | 4.35* |
| 88 | CF₃ | amino | H | H | methoxy | 3,5-dichloro-4-methoxyphenyl | |
| 89 | CF₃ | amino | H | H | methoxy | 3,4-dimethoxy-5-(trifluoromethyl)phenyl | 3.56* |
| 90 | CF₃ | amino | H | H | methoxy | 3,5-dichloro-4-methylphenyl | |
| 91 | CF₃ | (pyridin-2-ylmethyl)amino | H | H | methoxy | 7-chloro-1,3-benzodioxol-5-yl | |
| 92 | CF₃ | (pyrazin-2-ylmethyl)amino | H | H | methoxy | 7-chloro-1,3-benzodioxol-5-yl | |
| 93 | CF₃ | prop-2-en-1-ylamino | H | H | methoxy | 7-chloro-1,3-benzodioxol-5-yl | |
| 94 | CF₃ | (2-methylprop-2-en-1-yl)amino | H | H | methoxy | 7-chloro-1,3-benzodioxol-5-yl | |
| 95 | CF₃ | (pyrazin-2-ylmethyl)amino | H | H | methoxy | 3-chloro-5-(trifluoromethyl)phenyl | |
| 96 | CF₃ | (2-methylprop-2-en-1-yl)amino | H | H | methoxy | 3-chloro-5-(trifluoromethyl)phenyl | |
| 97 | CF₃ | prop-2-en-1-ylamino | H | H | methoxy | 3-chloro-5-(trifluoromethyl)phenyl | |
| 98 | CF₃ | (pyridin-2-ylmethyl)amino | H | H | methoxy | 3-chloro-5-(trifluoromethyl)phenyl | |
| 99 | pentafluoroethyl | (pyrazin-2-ylmethyl)amino | H | H | methoxy | 3-chloro-5-(trifluoromethyl)phenyl | |
| 100 | pentafluoroethyl | (2-methylprop-2-en-1-yl)amino | H | H | methoxy | 3-chloro-5-(trifluoromethyl)phenyl | |
| 101 | pentafluoroethyl | prop-2-en-1-ylamino | H | H | methoxy | 3-chloro-5-(trifluoromethyl)phenyl | |
| 102 | pentafluoroethyl | (pyridin-2-ylmethyl)amino | H | H | methoxy | 3-chloro-5-(trifluoromethyl)phenyl | |
| 103 | CF₃ | diprop-2-en-1-ylamino | H | H | methoxy | 3-chloro-5-(trifluoromethyl)phenyl | 4.08* |
| 104 | CF₃ | bis(2-methylprop-2-en-1-yl)amino | H | H | methoxy | 3-chloro-5-(trifluoromethyl)phenyl | 5.22* |
| 105 | CF₃ | diprop-2-yn-1-ylamino | H | H | methoxy | 3-chloro-5-(trifluoromethyl)phenyl | 4.91* |
| 106 | CF₃ | methylamino | H | H | methoxy | 3-chloro-5-(trifluoromethyl)phenyl | 4.51* |
| 107 | CF₃ | dimethylamino | H | H | methoxy | 3-chloro-5-(trifluoromethyl)phenyl | 5.11* |
| 108 | CF₃ | bis[(6-methylpyridin-2-yl)methyl]amino | H | H | methoxy | 3-chloro-5-(trifluoromethyl)phenyl | 3.79* |
| 109 | difluoromethyl | amino | H | H | methoxy | 7-chloro-1,3-benzodioxol-5-yl | |
| 110 | 1-fluoroethyl | amino | H | H | methoxy | 7-chloro-1,3-benzodioxol-5-yl | |
| 111 | propyl | amino | H | H | methoxy | 7-chloro-1,3-benzodioxol-5-yl | |
| 112 | cyano | amino | H | H | methoxy | 7-chloro-1,3-benzodioxol-5-yl | |
| 113 | dimethoxymethyl | amino | H | H | methoxy | 7-chloro-1,3-benzodioxol-5-yl | |
| 114 | (Z)-(methoxyimino)methyl | amino | H | H | methoxy | 7-chloro-1,3-benzodioxol-5-yl | |
| 115 | (Z)-(hydroxyimino)methyl | amino | H | H | methoxy | 7-chloro-1,3-benzodioxol-5-yl | |
| 116 | 1,1,2,2-tetrafluoroethyl | amino | H | H | methoxy | 3,4,5-trichlorophenyl | 4.37** |
| 117 | CF₃ | amino | H | H | methoxy | 7-bromo-2,3-dihydro-1-benzofur-5-yl | |
| 118 | CF₃ | amino | H | H | methoxy | 7-chloro-2-methyl-2,3-dihydro-1-benzofur-5-yl | |
| 119 | CF₃ | amino | H | H | methoxy | 7-chloro-2,2-dimethyl-2,3-dihydro-1-benzofur-5-yl | |
| 120 | CF₃ | amino | H | H | methoxy | 7-chloro-2,2-dimethyl-1,3-benzodioxol-5-yl | |
| 121 | CF₃ | amino | H | H | methoxy | 3,5-dichloro-4-(dimethylamino)phenyl | 4.46* |
| 122 | CF₃ | amino | H | H | methoxy | 3-chloro-4-(dimethylamino)phenyl | 3.19* |

TABLE 1-continued

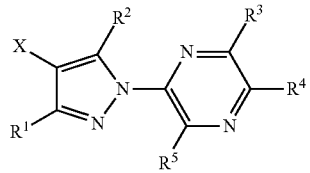

(I)

| Ex. | R¹ | R² | R³ | R⁴ | R⁵ | X | log P |
|---|---|---|---|---|---|---|---|
| 123 | CF₃ | amino | H | H | methoxy | 3-chloro-4-(dimethylamino)-5-(trifluoromethyl)phenyl | 4.72* |
| 124 | CF₃ | amino | H | H | methoxy | 3-chloro-5-fluoro-4-methoxyphenyl | 3.5***; 3.47* |
| 125 | CF₃ | amino | H | H | methoxy | 3-methoxy-4-(2,2,2-trifluoroethoxy)phenyl | 3.07* |
| 126 | CF₃ | amino | H | H | methoxy | 3-methoxy-4-(propan-2-yloxy)-5-(trifluoromethyl)phenyl | 4.28* |
| 127 | CF₃ | amino | H | H | methoxy | 3-ethoxy-4-(2,2,2-trifluoroethoxy)phenyl | 3.68* |
| 128 | CF₃ | amino | H | H | methoxy | 2-bromo-3,4-dimethoxyphenyl | 2.87* |
| 129 | CF₃ | amino | H | H | bromine | 3-chloro-5-(trifluoromethyl)phenyl | 4.27* |
| 130 | CF₃ | amino | H | H | CF₃ | 3-chloro-5-(trifluoromethyl)phenyl | 4.57* |
| 131 | CF₃ | amino | H | H | methoxy | 9-bromo-3,4-dihydro-2H-1,5-benzodioxepin-7-yl | 3.32* |
| 132 | CF₃ | amino | H | H | methoxy | 8-bromo-2,3-dihydro-1,4-benzodioxin-6-yl | 3.09* |
| 133 | CF₃ | amino | H | H | methoxy | 8-chloro-2,3-dihydro-1,4-benzodioxin-6-yl | 3.02* |
| 134 | CF₃ | amino | H | H | methoxy | 3-chloro-5-methoxy-4-(2,2,2-trifluoroethoxy)phenyl | 3.88* |
| 135 | CF₃ | amino | H | H | methoxy | 8-chloro-4H-1,3-benzodioxin-6-yl | 3.02* |
| 136 | CF₃ | amino | H | H | methoxy | 9-chloro-3,4-dihydro-2H-1,5-benzodioxepin-7-yl | 3.25* |
| 137 | CF₃ | amino | H | H | methoxy | 2-bromophenyl | 3* |
| 138 | CF₃ | amino | H | H | methoxy | 2-iodophenyl | 3.09* |
| 139 | CF₃ | amino | H | H | methoxy | 7-iodo-1,3-benzodioxol-5-yl | 3.27* |
| 140 | CF₃ | amino | H | H | methoxy | 3-bromo-5-ethoxy-4-(2,2,2-trifluoroethoxy)phenyl | 4.3* |
| 141 | CF₃ | amino | H | H | methoxy | 3-chloro-4,5-dimethoxyphenyl | 3.22* |
| 142 | CF₃ | amino | H | H | methoxy | 2,3-dichloro-6-fluorophenyl | 3.31* |
| 143 | CF₃ | amino | H | H | methoxy | 6-chloro-1,3-benzodioxol-5-yl | 2.86* |
| 144 | CF₃ | amino | H | H | methoxy | 3-chloro-5-ethoxy-4-(2,2,2-trifluoroethoxy)phenyl | 4.21* |
| 145 | CF₃ | amino | H | H | methoxy | 2,2-dimethyl-3,4-dihydro-2H-chromen-6-yl | 3.68* |
| 146 | CF₃ | amino | H | H | methoxy | 3-bromo-4,5-dimethoxyphenyl | |
| 147 | CF₃ | amino | H | H | methoxy | 3-iodo-4,5-dimethoxyphenyl | 3.47* |
| 148 | CF₃ | amino | H | H | methoxy | 3-fluoro-4,5-dimethoxyphenyl | |
| 149 | CF₃ | amino | H | H | methoxy | 3-cyano-4,5-dimethoxyphenyl | |
| 150 | CF₃ | amino | H | H | methoxy | 7-cyano-1,3-benzodioxol-5-yl | 2.66* |
| 151 | CF₃ | amino | H | H | methoxy | 7-cyano-2,3-dihydro-1-benzofur-5-yl | |
| 152 | 2-fluoropropan-2-yl | amino | H | H | methoxy | 3,4-dimethoxy-5-(trifluoromethyl)phenyl | |
| 153 | CH₃ | amino | H | H | methoxy | 3,4-dimethoxy-5-(trifluoromethyl)phenyl | |
| 154 | ethyl | amino | H | H | methoxy | 3,4-dimethoxy-5-(trifluoromethyl)phenyl | |
| 155 | propan-2-yl | amino | H | H | methoxy | 3,4-dimethoxy-5-(trifluoromethyl)phenyl | |
| 156 | cyclopropyl | amino | H | H | methoxy | 3,4-dimethoxy-5-(trifluoromethyl)phenyl | |
| 157 | 1,1,2,2-tetrafluoroethyl | amino | H | H | methoxy | 3,4-dimethoxy-5-(trifluoromethyl)phenyl | 3.58* |
| 158 | pentafluoroethyl | amino | H | H | methoxy | 3,4-dimethoxy-5-(trifluoromethyl)phenyl | |
| 159 | 2-fluoropropan-2-yl | amino | H | H | methoxy | 3-chloro-4,5-dimethoxyphenyl | |
| 160 | CH₃ | amino | H | H | methoxy | 3-chloro-4,5-dimethoxyphenyl | |
| 161 | ethyl | amino | H | H | methoxy | 3-chloro-4,5-dimethoxyphenyl | 2.66* |
| 162 | propan-2-yl | amino | H | H | methoxy | 3-chloro-4,5-dimethoxyphenyl | |
| 163 | cyclopropyl | amino | H | H | methoxy | 3-chloro-4,5-dimethoxyphenyl | |
| 164 | 1,1,2,2-tetrafluoroethyl | amino | H | H | methoxy | 3-chloro-4,5-dimethoxyphenyl | |

TABLE 1-continued (I)

| Ex. | R¹ | R² | R³ | R⁴ | R⁵ | X | log P |
|---|---|---|---|---|---|---|---|
| 165 | $CF_3$ | amino | H | H | methoxy | 2,4-dichloro-3-methylsulphanylphenyl | 4.14* |
| 166 | $CF_3$ | amino | H | H | methoxy | 2,4-dichloro-5-fluorophenyl | 3.66* |
| 167 | prop-1-en-2-yl | amino | H | H | methoxy | 3,5-dichlorophenyl | 3.79* |
| 168 | 2-fluoropropan-2-yl | amino | H | H | methoxy | 3,5-dichlorophenyl | 3.77* |
| 169 | difluorochloromethyl | amino | H | H | methoxy | 7-chloro-1,3-benzodioxol-5-yl | 3.26* |
| 170 | ethyl | amino | H | H | ethoxy | 7-chloro-1,3-benzodioxol-5-yl | 2.96* |
| 171 | $CF_3$ | amino | H | H | ethoxy | 7-chloro-1,3-benzodioxol-5-yl | 3.48* |
| 172 | $CF_3$ | amino | H | H | ethoxy | 7-cyano-1,3-benzodioxol-5-yl | 3.01* |
| 173 | $CF_3$ | amino | H | H | methoxy | 8-(trifluoromethyl)-2,3-dihydro-1,4-benzodioxin-6-yl | 3.27* |
| 174 | $CF_3$ | amino | H | H | methoxy | 7-fluoro-1,3-benzodioxol-5-yl | 2.91* |
| 175 | $CF_3$ | amino | H | H | ethoxy | 7-fluoro-1,3-benzodioxol-5-yl | 3.27* |
| 176 | $CF_3$ | amino | H | H | methoxy | 3-iodo-4,5-dimethoxyphenyl | 3.87* |
| 177 | ethyl | amino | H | H | ethoxy | 7-bromo-1,3-benzodioxol-5-yl | 3.03* |
| 178 | ethyl | amino | H | H | methoxy | 7-bromo-1,3-benzodioxol-5-yl | 2.65* |
| 179 | $CF_3$ | amino | H | H | methoxy | 2,4-dichloro-5-[(2,2,2-trifluoroethyl)sulphanyl]phenyl | 4.14* |
| 180 | $CF_3$ | amino | H | H | methoxy | 3,4-dichloro-5-[(2,2,2-trifluoroethyl)sulphanyl]phenyl | 4.43* |
| 181 | $CF_3$ | amino | H | H | methoxy | 2-chloro-4-fluoro-5-[(2,2,2-trifluoroethyl)sulphanyl]phenyl | |
| 182 | $CF_3$ | amino | H | H | methoxy | 3,4-dichloro-5-[(2,2,2-trifluoroethyl)sulphinyl]phenyl | 3.69* |

The logP values were determined in accordance with EEC Directive 79/831 Annex V.A8 by HPLC (High Performance Liquid Chromatography) using reversed-phase columns (C 18) by the following methods:
*The LC-MS determination within the acidic range is effected at pH 2.7 with 0.1% aqueous formic acid and acetonitrile (contains 0.1% formic acid) as the eluent; linear gradient from 10% acetonitrile to 95% acetonitrile.
**The determination is effected in the acidic range at pH 2.3 with 0.1% aqueous phosphoric acid and acetonitrile as the eluent; linear gradient from 10% acetonitrile to 95% acetonitrile.
***The LC-MS determination in the neutral range is effected at pH 7.8 with 0.001 molar aqueous ammonium hydrogencarbonate solution and acetonitrile as the eluent; linear gradient from 10% acetonitrile to 95% acetonitrile.

The calibration is effected with unbranched alkan-2-ones (having 3 to 16 carbon atoms) with known logP values (logP values determined on the basis of the retention times by linear interpolation between two successive alkanones).

The lambda max values were determined in the maxima of the chromatographic signals using the UV spectra from 200 nm to 400 nm.

NMR Data

Ex. 2: $^1$H NMR (300 MHz, CDCl$_3$), δ 8.21 (d, 1H), 8.08 (d, 1H), 7.58 (d, 2H), 7.28 (d, 2H), 4.71 (bs, 2H, NH$_2$), 4.10 (s, 3H).

Ex. 3: $^1$H NMR (300 MHz, CDCl$_3$), δ 8.14 (d, 1H), 8.05 (d, 1H), 7.58 (d, 1H), 7.47 (d, 1H), 7.34 (dd, 1H), 4.60 (bs, 2H, NH$_2$), 4.21 (tr, 1H), 4.08 (s, 3H), 3.36 (s, 3H), 1.71 (m, 2H), 0.87 (tr, 3H).

Ex. 4: $^1$H NMR (300 MHz, CDCl$_3$), δ 8.17 (d, 1H), 8.05 (d, 1H), 7.59 (d, 2H), 7.29 (d, 2H), 4.72 (bs, 2H, NH$_2$), 4.42 (tr, 2H), 1.85 (m, 2H), 1.07 (tr, 3H).

Ex. 5: $^1$H NMR (400 MHz, DMSO-d6), δ 8.44 (d, 1H), 8.25 (d, 1H), 7.63 (d, 2H), 7.31 (d, 2H), 5.84 (bs, 2H, NH$_2$), 4.46 (qu, 2H), 1.30 (tr, 3H).

Ex. 6: $^1$H NMR (400 MHz, DMSO-d6), δ 8.45 (d, 1H), 8.26 (d, 1H), 7.53 (s, 1H), 7.35 (s, 2H), 5.86 (bs, 2H, NH$_2$), 4.00 (s, 3H).

Ex. 7: $^1$H NMR (400 MHz, DMSO-d6), δ 8.73 (s, 2H), 7.50 (d, 2H), 7.39 (d, 2H), 5.87 (bs, 2H, NH$_2$).

Ex. 8: $^1$H NMR (400 MHz, DMSO-d6), δ 8.23 (d, 1H), 8.12 (d, 1H), 7.37 (s, 1H), 7.34 (s, 2H), 6.61-6.53 (dd, 1H), 5.73-5.68 (dd, 1H), 5.28-5.25 (dd, 1H), 4.71 (bs, 2H, NH$_2$), 4.03 (s, 3H).

Ex. 9: $^1$H NMR (400 MHz, DMSO-d6), δ 8.26 (d, 1H), 8.15 (d, 1H), 7.66 (s, 2H), 7.62 (s, 1H), 6.61-6.54 (dd, 1H), 5.73-5.68 (dd, 1H), 5.29-5.26 (dd, 1H), 4.83 (bs, 2H, NH$_2$), 4.02 (s, 3H).

Ex. 10: $^1$H NMR (400 MHz, DMSO-d6), δ 4.04 (s, 3H), 5.91 (bs, 2H), 7.59 (s, 1H), 7.68 (s, 1H), 7.76 (s, 1H), 8.26 (d, 1H), 8.45 (d, 1H).

Ex. 11: $^1$H NMR (400 MHz, CDCl$_3$), δ 7.88 (m, 2H), 7.86 (m, 1H), 7.83 (d, 1H), 7.59 (d, 1H), 6.06 (bs, 2H, NH$_2$), 4.27 (s, 3H).

Ex. 12: $^1$H NMR (400 MHz, DMSO-d6), δ 1.33 (t, 3H), 4.49 (q, 2H), 5.91 (bs, 2H), 7.59 (s, 1H), 7.68 (s, 1H); 7.76 (s, 1H); 8.24 (d, 1H); 8.42 (d, 1H).

Ex. 13: $^1$H NMR (400 MHz, DMSO-d6), δ 1.33 (d, 6H), 5.34 (m, 1H), 5.90 (bs, 2H), 7.58 (s, 1H), 7.67 (s, 1H), 7.76 (s, 1H), 8.22 (d, 1H), 8.41 (d, 1H).

Ex. 14: $^1$H NMR (400 MHz, DMSO-d6), δ 4.01 (s, 3H), 5.97 (bs, 2H), 7.95 (s, 2H), 8.00 (s, 1H), 8.27 (d, 1H), 8.46 (d, 1H).

Ex. 15: $^1$H NMR (400 MHz, DMSO-d6), δ 4.00 (s, 3H), 5.85 (bs, 2H); 7.57 (s, 1H), 7.66 (s, 1H), 7.77 (s, 1H), 8.27 (d, 1H), 8.45 (d, 1H).

Ex. 16: $^1$H NMR (400 MHz, DMSO-d6), δ 6.14 (bs, 2H), 7.60 (s, 1H), 7.69 (s, 1H), 7.78 (s, 1H), 8.75 (s, 2H).

Ex. 17: $^1$H NMR (400 MHz, DMSO-d6), δ 4.01 (s, 3H), 5.85 (bs, 2H), 7.61 (s, 1H), 7.69 (s, 1H), 7.76 (s, 1H), 8.26 (d, 1H), 8.45 (d, 1H).

Ex. 18: $^1$H NMR (400 MHz, DMSO-d6), δ 4.00 (s, 3H), 5.85 (bs, 2H), 7.65 (dd, 1H), 7.73-7.77 (m, 2H), 8.26 (d, 1H), 8.45 (d, 1H).

Ex. 19: ¹H NMR (400 MHz, DMSO-d6), δ 6.78 (bs, 2H), 7.60 (s, 1H), 7.70 (s, 1H), 7.82 (s, 1H), 8.78 (d, 1H), 9.13 (d, 1H).

Ex. 20: ¹H NMR (400 MHz, DMSO-d6), δ 1.92 (t, 3H), 3.99 (s, 3H), 5.60 (bs, 2H), 7.66-7.72 (m, 2H), 7.79 (s, 1H), 8.24 (d, 1H), 8.40 (d, 1H).

Ex. 21: ¹H NMR (400 MHz, DMSO-d6), δ 4.00 (s, 3H), 5.83 (bs, 2H), 7.46-7.48 (m, 2H), 7.58 (d, 1H), 8.27 (d, 1H), 8.45 (d, 1H).

Ex. 22: ¹H NMR (400 MHz, DMSO-d6), δ 4.00 (s, 3H), 5.84 (bs, 2H), 7.51 (d, 2H), 7.76 (t, 1H), 8.26 (d, 1H), 8.46 (d, 1H).

Ex. 23: ¹H NMR (400 MHz, DMSO-d6), δ 2.53 (s, 3H), 6.03 (bs, 2H), 7.61 (s, 1H), 7.70 (s, 1H), 7.78 (s, 1H), 8.53 (d, 1H), 8.71 (d, 1H).

Ex. 24: ¹H NMR (400 MHz, DMSO-d6), δ 2.46 (s, 3H), 2.54 (s, 3H), 5.97 (bs, 2H), 7.61 (s, 1H), 7.71 (s, 1H), 7.77 (s, 1H), 8.60 (s, 1H).

Ex. 25: ¹H NMR (400 MHz, DMSO-d6), δ 2.83 (s, 6H), 5.89 (bs, 2H), 7.57 (s, 1H), 7.66 (s, 1H), 7.76 (s, 1H), 7.87 (d, 1H), 8.30 (d, 1H).

Ex. 27: ¹H NMR (400 MHz, DMSO-d6), δ 7.81 (s, 2H), 7.94 (s, 1H), 8.06 (bs, 2H), 8.98 (d, 1H), 9.06 (d, 1H).

Ex. 28: ¹H NMR (400 MHz, DMSO-d6), δ 2.52 (s, 3H), 6.18 (bs, 2H), 7.59 (s, 1H), 7.69 (s, 1H), 7.78 (s, 1H), 8.35 (d, 1H), 8.68 (d, 1H).

Ex. 29: ¹H NMR (400 MHz, DMSO-d6), δ 2.93 (s, 3H), 6.74 (bs, 2H), 7.61 (s, 1H), 7.71 (s, 1H), 7.81 (s, 1H), 8.74 (d, 1H), 8.93 (d, 1H).

Ex. 30: ¹H NMR (400 MHz, DMSO-d6), δ 3.40 (s, 3H), 6.14 (bs, 2H), 7.57 (s, 1H), 7.66 (s, 1H), 7.78 (s, 1H), 9.03 (d, 1H), 9.05 (d, 1H).

Ex. 31: ¹H NMR (400 MHz, DMSO-d6), δ 5.90 (bs, 2H), 6.54 (dd, 1H), 7.54 (s, 1H), 7.62 (s, 1H), 7.68 (dd, 1H), 7.75 (s, 1H), 8.35 (dd, 1H), 8.73 (d, 1H), 8.81 (d, 1H).

Ex. 32: ¹H NMR (400 MHz, DMSO-d6), δ 3.87 (s, 4H), 4.03 (s, 3H), 6.93-6.95 (m, 5H), 7.05 (s, 1H), 7.21-7.24 (m, 6H), 7.81 (s, 1H), 8.41 (d, 1H), 8.59 (d, 1H).

Ex. 33: ¹H NMR (400 MHz, DMSO-d6), δ 3.91 (d, 2H), 4.00 (s, 3H), 6.42 (t, 1H), 6.82-6.84 (m, 2H), 7.13-7.17 (m, 3H), 7.40 (s, 1H), 7.48 (s, 1H), 7.74 (s, 1H), 8.30 (d, 1H), 8.47 (d, 1H).

Ex. 34: ¹H NMR (400 MHz, DMSO-d6), δ 1.30 (t, 3H), 3.88 (s, 4H), 4.52 (q, 2H), 6.90 (s, 1H), 6.94-6.97 (m, 4H), 6.99 (s, 1H), 7.21-7.24 (m, 6H), 7.80 (s, 1H), 8.40 (d, 1H), 8.57 (d, 1H).

Ex. 35: ¹H NMR (400 MHz, DMSO-d6), δ 1.33 (t, 3H), 3.92 (d, 2H), 4.48 (q, 2H), 6.40 (t, 1H), 6.82-6.85 (m, 2H), 7.12-7.16 (m, 3H), 7.37 (s, 1H), 7.46 (s, 1H), 7.73 (s, 1H), 8.28 (d, 1H), 8.45 (d, 1H).

Ex. 36: ¹H NMR (400 MHz, DMSO-d6), δ 1.29 (t, 3H), 3.89 (s, 4H), 4.51 (q, 2H), 6.96 (d, 4H), 6.99 (s, 1H), 7.08 (s, 1H), 7.27 (d, 4H), 7.83 (s, 1H), 8.39 (d, 1H), 8.57 (d, 1H).

Ex. 37: ¹H NMR (400 MHz, DMSO-d6), δ 1.33 (t, 3H), 3.92 (d, 2H), 4.48 (q, 2H), 6.46 (t, 1H), 6.84 (d, 2H), 7.18 (d, 2H), 7.37 (s, 1H), 7.47 (s, 1H), 7.73 (s, 1H), 8.28 (d, 1H), 8.45 (d, 1H).

Ex. 38: ¹H NMR (400 MHz, DMSO-d6), δ 3.88 (s, 4H), 4.03 (s, 3H), 6.95 (d, 4H), 7.03 (s, 1H), 7.13 (s, 1H), 7.27 (d, 4H), 7.83 (s, 1H), 8.40 (d, 1H), 8.59 (d, 1H).

Ex. 39: ¹H NMR (400 MHz, DMSO-d6), δ 3.91 (d, 2H), 4.01 (s, 3H), 6.47 (t, 1H), 6.84 (d, 2H), 7.20 (d, 2H), 7.39 (s, 1H), 7.49 (s, 1H), 7.74 (s, 1H), 8.30 (d, 1H), 8.48 (d, 1H).

Ex. 40: ¹H NMR (400 MHz, DMSO-d6), δ 1.33 (t, 3H), 3.69 (s, 3H), 3.83 (d, 2H), 4.48 (q, 2H), 6.46 (t, 1H), 6.84 (d, 2H), 7.18 (d, 2H), 7.37 (s, 1H), 7.47 (s, 1H), 7.73 (s, 1H), 8.28 (d, 1H), 8.45 (d, 1H).

Ex. 41: ¹H NMR (400 MHz, DMSO-d6), δ 3.72 (s, 3H), 3.85 (d, 2H), 4.02 (s, 3H), 6.35 (t, 1H), 6.72-6.77 (m, 4H), 7.43 (s, 1H), 7.51 (s, 1H), 7.78 (s, 1H), 8.32 (d, 1H), 8.50 (d, 1H).

Ex. 42: ¹H NMR (400 MHz, DMSO-d6), δ 3.73 (s, 6H), 3.76 (s, 4H), 4.04 (s, 3H), 6.79 (d, 4H), 6.86 (d, 4H), 6.92 (s, 1H), 7.05 (s, 1H), 7.80 (s, 1H), 8.42 (d, 1H), 8.60 (d, 1H).

Ex. 43: ¹H NMR (400 MHz, DMSO-d6), δ 1.30 (t, 3H), 3.73 (s, 6H), 3.77 (s, 4H), 4.52 (q, 2H), 6.79 (d, 2H), 6.86-6.88 (m, 3H), 7.00 (s, 1H), 7.79 (s, 1H), 8.40 (d, 1H), 8.58 (d, 1H).

Ex. 44: ¹H NMR (400 MHz, DMSO-d6), δ 6.13 (bs, 2H), 7.09 (dd, 1H), 7.17 (dd, 1H), 7.56 (s, 1H), 7.64 (s, 1H), 7.75 (dd, 1H), 7.79 (s, 1H), 8.78 (d, 1H), 8.87 (d, 1H).

Ex. 45: ¹H NMR (400 MHz, DMSO-d6), δ 5.95 (bs, 2H), 7.54 (s, 1H), 7.62 (s, 1H), 7.75 (s, 1H), 7.80 (dd, 1H), 8.46 (dd, 1H), 8.75 (d, 1H), 8.81 (d, 1H).

Ex. 46: ¹H NMR (400 MHz, DMSO-d6), δ 8.45 (d, 1H), 8.27 (d, 1H), 7.78 (s, 1H), 7.64 (s, 1H), 7.54 (s, 1H), 5.81 (bs, 2H, NH₂), 4.00 (s, 3H).

Ex. 47: ¹H NMR (400 MHz, DMSO-d6), δ 8.43 (d, 1H), 8.25 (d, 1H), 7.73 (s, 1H), 7.62 (s, 1H), 7.56 (s, 1H), 5.64 (bs, 2H, NH₂), 3.99 (s, 1H), 3.58 (s, 3H).

Ex. 48: ¹H NMR (400 MHz, DMSO-d6), δ 4.00 (s, 3H), 5.60 (bs, 2H), 6.15 (s, 2H), 6.83-6.84 (m, 2H), 8.24 (d, 1H), 8.42 (d, 1H).

Ex. 49: ¹H NMR (400 MHz, DMSO-d6), δ 4.00 (s, 3H), 6.83 (bs, 2H), 7.21 (dd, 1H), 7.48 (d, 1H), 7.84 (dd, 1H), 8.28 (d, 1H), 8.46 (d, 1H), 8.59 (dd, 1H).

Ex. 50: ¹H NMR (400 MHz, DMSO-d6), δ 4.01 (s, 3H), 5.92 (bs, 2H), 7.95 (d, 1H), 8.26 (d, 1H), 8.44 (d, 1H), 8.52 (d, 1H), 8.65 (d, 1H).

Ex. 51: ¹H NMR (400 MHz, DMSO-d6), δ 8.43 (d, 1H), 8.25 (d, 1H), 6.94 (s, 2H), 5.60 (bs, 2H, NH₂), 3.99 (s, 3H), 3.86 (s, 3H), 3.81 (s, 3H).

Ex. 52: ¹H NMR (400 MHz, DMSO-d6), δ 4.00 (s, 3H), 5.80 (bs, 2H), 8.23 (d, 1H), 8.25 (d, 1H), 8.43 (d, 1H), 8.64 (d, 1H).

Ex. 53: ¹H NMR (400 MHz, DMSO-d6), δ 4.00 (s, 3H), 6.75 (bs, 2H), 7.49 (d, 1H), 7.95 (dd, 1H), 8.28 (d, 1H), 8.47 (d, 1H), 8.62 (d, 1H).

Ex. 54: ¹H NMR (400 MHz, DMSO-d6), δ 3.99 (s, 3H), 6.65 (bs, 2H), 7.53 (d, 1H), 7.95 (dd, 1H), 8.28 (d, 1H), 8.47 (d, 1H), 8.62 (d, 1H).

Ex. 55: ¹H NMR (400 MHz, DMSO-d6), δ 4.01 (s, 3H), 6.78 (bs, 2H), 7.64 (s, 1H), 7.72 (s, 1H), 8.30 (d, 1H), 8.49 (d, 1H).

Ex. 56: ¹H NMR (400 MHz, DMSO-d6), δ 8.74 (app. s, 2H), 7.54 (t, 1H, J=1.9 Hz), 7.34 (d, 2H, J=1.9 Hz), 6.08 (bs, 2H, NH₂).

Ex. 57: ¹H NMR (400 MHz, DMSO-d6), δ 4.00 (s, 3H), 5.74 (bs, 2H), 7.46 (dd, 1H), 7.81 (dd, 1H), 8.24 (d, 1H), 8.41-8.43 (m, 2H).

Ex. 58: ¹H NMR (400 MHz, DMSO-d6), δ 4.00 (s, 3H), 5.80 (bs, 2H), 7.55 (d, 1H), 7.78 (dd, 1H), 8.26 (d, 1H), 8.34 (d, 1H), 8.44 (d, 1H).

Ex. 59: ¹H NMR (400 MHz, DMSO-d6), δ 8.44 (d, 1H), 8.26 (d, 1H), 7.74 (s, 1H), 7.67 (s, 1H), 7.60 (s, 1H), 6.80-6.55 (tt, 1H, CHF₂), 5.83 (bs, 2H, NH₂), 4,00 (s, 3H).

Ex. 65: ¹H NMR (400 MHz, DMSO-d6), δ 8.41 (d, 1H), 8.24 (d, 1H), 6.84 (s, 1H), 6.83 (s, 1H), 6.75-6.49 (tt, 1H, CHF₂), 6.15 (s, 2H), 5.53 (bs, 2H, NH₂), 3.99 (s, 3H).

Ex. 66: ¹H NMR (400 MHz, DMSO-d6), δ 8.41 (d, 1H), 8.24 (d, 1H), 7.15 (s, 1H), 7.08 (s, 1H), 6.74-6.48 (tt, 1H, CHF₂), NH₂ broad signal, 4.68-4.64 (dd, 2H), 3.99 (s, 3H), 3.34-3.29 (dd, 2H).

Ex. 74: ¹H NMR (400 MHz, DMSO-d6), δ 8.45 (d, 1H), 8.26 (d, 2H), 6.95 (s, 1H), 6.87 (s, 1H), 6.17 (s, 2H), 5.80 (s, 2H), 3.98 (s, 3H).

Ex. 75: ¹H NMR (400 MHz, DMSO-d6), δ 8.27 (d, 1H), 8.15 (d, 1H), 6.87 (s, 1H), 6.84 (s, 1H), 6.11 (s, 2H), 5.21 (bs, 2H, NH$_2$), 3.96 (s, 3H), 2.11 (s, 3H).

Ex. 76: ¹H NMR (400 MHz, DMSO-d6), δ 8.28 (d, 1H), 8.16 (d, 1H), 6.85 (s, 1H), 6.82 (s, 1H), 6.12 (s, 2H), 5.14 (bs, 2H, NH$_2$), 3.97 (s, 3H), 2.56-2.49 (q, 2H), 1.08 (t, 3H).

Ex. 77: ¹H NMR (400 MHz, DMSO-d6), δ 8.31 (d, 1H), 8.18 (d, 1H), 6.85 (s, 1H), 6.82 (s, 1H), 6.15 (s, 2H), 5.21 (bs, 2H, NH$_2$), 3.96 (s, 3H), 2.98-2.93 (m, 1H), 1.11 (d, 3H).

Ex. 79: ¹H NMR (400 MHz, DMSO-d6), δ 8.31 (d, 1H), 8.17 (d, 1H), 6.98 (s, 1H), 6.95 (s, 1H), 6.14 (s, 2H), 5.34 (bs, 2H, NH$_2$), 3.97 (s, 3H), 1.77-1.73 (m, 1H), 0.81-0.73 (m, 4H).

Ex. 86: ¹H NMR (400 MHz, DMSO-d6), δ 8.49 (d, 1H), 8.29 (d, 1H), 7.89 (d, 1H), 7.72 (d, 1H), 6.18 (bs, 2H), 3.99 (s, 3H).

Ex. 87: ¹H NMR (400 MHz, DMSO-d6), δ 8.44 (d, 1H), 8.26 (d, 1H), 7.54 (s, 2H), 5.91 (bs, 2H, NH$_2$), 4.00 (s, 3H).

Ex. 89: ¹H NMR (400 MHz, DMSO-d6), δ 8.48 (d, 1H), 8.28 (d, 1H), 7.30 (s, 1H), 7.10 (s, 1H), 5.93 (bs, 2H, NH$_2$), 3.99 (s, 3H), 3.93 (s, 3H), 3.86 (s, 3H).

Ex. 96: ¹H NMR (400 MHz, DMSO-d6), δ 8.47 (d, 1H), 8.28 (d, 1H), 7.83 (s, 1H), 7.70 (s, 1H), 7.59 (s, 1H), 6.15 (br t, 1H), 4.65 (br s, 1H), 4.60 (br. s, 1H), 4.00 (s, 3H), 3.18 (d, 2H), 1.25 (s, 3H).

Ex. 103: ¹H NMR (400 MHz, CDCl$_3$), δ 7.82 (d, 1H), 7.67 (m, 1H), 7.63 (m, 2H), 7.60 (d, 1H), 6.09 (bs, 2H, NH$_2$), 4.25 (s, 3H).

Ex. 105: ¹H NMR (400 MHz, DMSO-d6), δ 8.53 (d, 1H), 8.32 (d, 1H), 7.89 (s, 1H), 7.87 (s, 1H), 7.79 (s, 1H), 4.00 (s, 3H), 3.67 (d, 4H), 2.96 (t, 2H).

Ex. 106: ¹H NMR (400 MHz, DMSO-d6), δ 8.53 (d, 1H), 8.32 (d, 1H), 7.89 (m, 1H), 7.87 (m, 1H), 7.78 (m, 1H), 4.00 (s, 3H), 3.67 (d, 4H), 2.96 (t, 2H).

Ex. 109: ¹H NMR (400 MHz, DMSO-d6), δ 8.50 (d, 1H), 8.28 (d, 1H), 7.80 (m, 1H), 7.49 (t, 2H), 7.42 (m, 2H), 7.04 (d, 2H), 6.85 (d, 2H), 4.06 (s, 4H), 3.91 (s, 3H), 2.33 (s, 6H).

Ex. 116: ¹H NMR (400 MHz, DMSO-d6), δ 8.47 (d, 1H), 8.28 (d, 1H), 7.55 (s, 2H), 7.91-6.62 (1H, m) 6.03 (bs, 2H), 3.98 (s, 3H).

Ex. 121: ¹H NMR (400 MHz, DMSO-d6), δ 8.47 (d, 1H), 8.28 (d, 1H), 7.34 (s, 2H), 5.97 (bs, 2H, NH$_2$), 3.98 (s, 3H), 2.86 (s, 6H).

Ex. 122: ¹H NMR (400 MHz, DMSO-d6), δ 8.46 (d, 1H), 8.27 (d, 1H), 7.33-7.21 (m, 3H), 5.77 (bs, 2H, NH$_2$), 3.99 (s, 3H), 2.77 (s, 6H).

Ex. 123: ¹H NMR (400 MHz, DMSO-d6), δ 8.48 (d, 1H), 8.29 (d, 1H), 7.67 (s, 1H), 7.56 (d, 1H), 6.08 (bs, 2H, NH$_2$), 3.99 (s, 3H), 2.83 (s, 6H).

Ex. 124: ¹H NMR (400 MHz, DMSO-d6), δ 8.47 (d, 1H), 8.28 (d, 1H), 7.24 (s, 1H), 7.22 (s, 1H), 5.96 (bs, 2H, NH$_2$), 3.99 (s, 3H), 3.93 (s, 3H).

Ex. 125: ¹H NMR (400 MHz, DMSO-d6), δ 8.46 (d, 1H), 8.27 (d, 1H), 7.15 (d, 1H), 6.99 (s, 1H), 6.90 (d, 1H), 5.72 (bs, 2H, NH$_2$), 4.75-4.69 (quat, 2H), 3.99 (s, 3H), 3.83 (s, 3H).

Ex. 126: ¹H NMR (400 MHz, DMSO-d6), δ 8.48 (d, 1H), 8.28 (d, 1H), 7.25 (s, 1H), 7.09 (s, 1H), 5.90 (bs, 2H, NH$_2$), 4.93-4.87 (m, 1H), 3.99 (s, 3H), 3.90 (s, 3H), 1.24 (d, 6H).

Ex. 127: ¹H NMR (400 MHz, DMSO-d6), δ 8.46 (d, 1H), 8.27 (d, 1H), 7.16 (s, 1H), 6.97 (d, 1H), 6.90 (d, 1H), 5.67 (bs, 2H, NH$_2$), 4.75-4.68 (quat, 2H), 4.12-4.09 (quat, 2H), 3.99 (s, 3H), 1.36 (t, 3H).

Ex. 128: ¹H NMR (400 MHz, DMSO-d6), δ 8.44 (d, 1H), 8.26 (d, 1H), 7.14 (d, 1H), 7.09 (d, 1H), 5.59 (bs, 2H, NH$_2$), 3.99 (s, 3H), 3.87 (s, 3H), 3.77 (s, 3H).

Ex. 129: ¹H NMR (400 MHz, DMSO-d6), δ 8.80 (d, 1H), 8.76 (d, 1H), 7.84 (s, 1H), 7.69 (s, 1H), 6.31 (bs, 2H, NH$_2$).

Ex. 130: ¹H NMR (400 MHz, DMSO-d6), δ 9.10 (s, 2H), 7.86 (s, 1H), 7.69 (s, 1H), 7.59 (s, 1H), 6.34 (bs, 2H, NH$_2$).

Ex. 131: ¹H NMR (400 MHz, DMSO-d6), δ 8.46 (d, 1H), 8.27 (d, 1H), 7.20 (d, 1H), 6.94 (d, 1H), 5.74 (bs, 2H), 4.21 (m, 2H), 3.98 (s, 3H), 2.18 (m, 2H).

Ex. 132: ¹H NMR (400 MHz, DMSO-d6), δ 8.45 (d, 1H), 8.26 (d, 1H), 7.06 (d, 1H), 6.84 (d, 1H), 5.76 (bs, 2H), 4.37 (m, 2H), 4.31 (m, 2H), 3.98 (s, 3H).

Ex. 133: ¹H NMR (400 MHz, DMSO-d6), δ 8.45 (d, 1H), 8.26 (d, 1H), 6.92 (d, 1H), 6.80 (d, 1H), 5.74 (bs, 2H), 4.37 (m, 2H), 4.32 (m, 2H), 3.98 (s, 3H).

Ex. 134: ¹H NMR (400 MHz, DMSO-d6), δ 8.47 (d, 1H), 8.28 (d, 1H), 7.02 (s, 1H), 6.99 (s, 1H), 5.90 (bs, 2H, NH$_2$), 4.69-4.82 (quat, 2H), 3.99 (s, 3H), 3.90 (s, 3H).

Ex. 135: ¹H NMR (400 MHz, DMSO-d6), δ 8.47 (d, 1H), 8.27 (d, 1H), 7.23 (s, 1H), 7.03 (s, 1H), 5.81 (bs, 2H, NH$_2$), 5.40 (s, 2H), 4.94 (s, 2H), 3.98 (s, 3H).

Ex. 136: ¹H NMR (400 MHz, DMSO-d6), δ 8.46 (d, 1H), 8.27 (d, 1H), 7.06 (d, 1H), 6.90 (d, 1H), 5.82 (bs, 2H, NH$_2$), 4.24 (m, 4H), 3.98 (s, 3H), 2.17 (m, 2H).

Ex. 137: ¹H NMR (400 MHz, CD$_3$CN), δ 8.32 (d, 1H), 8.18 (d, 1H), 7.75 (dd, 1H), 7.44 (m, 2H), 7.35 (m, 1H), 4.77 (bs, 2H), 4.04 (s, 3H).

Ex. 138: ¹H NMR (400 MHz, DMSO-d6), δ 8.44 (d, 1H), 8.26 (d, 1H), 7.95 (m, 1H), 7.47 (m, 1H), 7.15 (m, 1H), 5.10 (bs, 2H), 3.99 (s, 3H).

Ex. 139: ¹H NMR (600 MHz, CD$_3$CN), δ 8.33 (d, 1H), 8.17 (d, 1H), 7.18 (d, 1H), 6.86 (d, 1H), 6.08 (bs, 2H), 4.83 (s, 2H), 4.03 (s, 3H).

Ex. 140: ¹H NMR (400 MHz, DMSO-d6), δ 8.47 (d, 1H), 8.28 (d, 1H), 7.12 (s, 1H), 7.02 (s, 1H), 5.88 (bs, 2H, NH$_2$), 4.68-4.61 (quat, 2H), 4.18-4.13 (quat, 2H), 3.99 (s, 3H), 1.38 (t, 3H).

Ex. 141: ¹H NMR (400 MHz, DMSO-d6), δ 8.47 (d, 1H), 8.27 (d, 1H), 6.96 (s, 2H), 5.87 (bs, 2H, NH$_2$), 3.99 (s, 3H), 3.87 (s, 3H), 3.80 (s, 3H).

Ex. 142: ¹H NMR (400 MHz, DMSO-d6), δ 8.46 (d, 1H), 8.27 (d, 1H), 7.77 (m, 1H), 7.41 (t, 1H), 6.00 (bs, 2H), 3.99 (s, 3H), 2.18 (m, 2H).

Ex. 143: ¹H NMR (400 MHz, DMSO-d6), δ 8.44 (d, 1H), 8.26 (d, 1H), 7.18 (s, 1H), 6.89 (s, 1H), 6.12 (s, 2H), 5.66 (s, 2H), 3.98 (bs, 2H, NH$_2$).

Ex. 144: ¹H NMR (400 MHz, DMSO-d6), δ 8.47 (d, 1H), 8.28 (d, 1H), 6.98 (s, 2H), 5.88 (bs, 2H, NH$_2$), 4.69-4.62 (quat, 2H), 4.18-4.13 (quat, 2H), 3.99 (s, 3H), 1.38 (t, 3H).

Ex. 145: ¹H NMR (400 MHz, DMSO-d6), δ 8.45 (d, 1H), 8.27 (d, 1H), 7.07 (s, 1H), 7.04 (d, 1H), 6.76 (d, 1H), 5.58 (bs, 2H, NH$_2$), 3.98 (s, 3H), 2.79-2.75 (dt, 2H), 1.80-1.77 (dt, 2H), 1.30 (s, 6H).

Ex. 147: ¹H NMR (400 MHz, DMSO-d6), δ 8.46 (d, 1H), 8.27 (d, 1H), 7.28 (s, 1H), 7.00 (s, 1H), 5.84 (bs, 2H, NH$_2$), 3.99 (s, 3H), 3.85 (s, 3H), 3.75 (s, 3H).

Ex. 150: ¹H NMR (400 MHz, DMSO-d6), δ 8.47 (d, 1H), 8.27 (d, 1H), 7.15 (s, 1H), 7.11 (s, 1H), 6.30 (s, 2H), 5.87 (bs, 2H, NH$_2$), 3.99 (s, 3H).

Ex. 157: ¹H NMR (400 MHz, DMSO-d6), δ 8.45 (d, 1H), 8.28 (d, 1H), 7.30 (s, 1H), 7.12 (s, 1H), 6.75 (tt, CHF$_2$), 5.84 (bs, 2H, NH$_2$), 3.98 (s, 3H), 3.92 (s, 3H), 3.86 (s, 3H).

Ex. 161: ¹H NMR (400 MHz, DMSO-d6), δ 8.32 (d, 1H), 8.19 (d, 1H), 6.95 (s, 2H), 5.37 (bs, 2H, NH$_2$), 3.96 (s, 3H), 3.87 (s, 3H), 3.77 (s, 3H), 2.59 (q, 2H), 1.08 (t, 3H).

Ex. 165: ¹H NMR (400 MHz, DMSO-d6), δ 8.45 (d, 1H), 8.27 (d, 1H), 7.81 (s, 1H), 7.66 (s, 1H), 5.85 (bs, 2H, NH$_2$), 3.99 (s, 3H), under solvents (s, 3H).

Ex. 166: ¹H NMR (400 MHz, DMSO-d6), δ 8.46 (d, 1H), 8.27 (d, 1H), 7.92 (d, 1H), 7.52 (d, 1H), 5.90 (bs, 2H, NH₂), 3.99 (s, 3H).

Ex. 167: ¹H NMR (400 MHz, DMSO-d6), δ 8.37 (d, 1H), 8.23 (d, 1H), 7.44 (s, 1H), 7.31 (s, 2H), 5.50 (bs, 2H, NH₂), 5.08 (s, 1H), 4.85 (s, 1H), 3.97 (s, 3H), 1.96 (s, 3H).

Ex. 168: ¹H NMR (400 MHz, DMSO-d6), δ 8.38 (d, 1H), 8.23 (d, 1H), 7.48 (s, 1H), 7.38 (s, 2H), 5.50 (bs, 2H, NH₂), 3.97 (s, 3H), 1.57 (s, 3H), 1.52 (s, 3H).

Ex. 169: ¹H NMR (400 MHz, DMSO-d6), δ 8.45 (d, 2H), 8.27 (d, 2H), 6.85 (s, 2H), 6.18 (s, 2H), 5.74 (bs, 2H, NH₂), 3.99 (s, 3H).

Ex. 170: ¹H NMR (400 MHz, DMSO-d6), δ 8.27 (d, 1H), 8.16 (d, 1H), 6.88 (s, 1H), 6.84 (s, 1H), 6.14 (s, 2H), 5.30 (bs, 2H, NH₂), 4.44 (q, 2H), 2.53 (q, 2H), 1.33 (t, 3H), 1.08 (t, 3H).

Ex. 171: ¹H NMR (400 MHz, DMSO-d6), δ 8.43 (d, 1H), 8.24 (d, 1H), 6.84 (s, 2H), 6.18 (s, 2H), 5.78 (s, 2H), 4.47 (q, 2H), 1.32 (t, 3H).

Ex. 172: ¹H NMR (400 MHz, DMSO-d6), δ 8.43 (d, 1H), 8.25 (d, 1H), 7.14 (s, 1H), 7.10 (s, 1H), 6.30 (s, 2H), 5.86 (bs, 2H, NH₂), 4.48 (q, 2H), 1.32 (t, 3H).

Ex. 173: ¹H NMR (400 MHz, DMSO-d6), δ 8.47 (d, 1H), 8.28 (d, 2H), 7.11 (s, 1H), 7.09 (s, 1H), 5.89 (bs, 2H, NH₂), 4.42-4.36 (m, 4H), 3.98 (s, 3H).

Ex. 174: ¹H NMR (400 MHz, DMSO-d6), δ 8.46 (d, 1H), 8.27 (d, 1H), 6.76 (s, 2H), 6.17 (s, 2H), 5.80 (bs, 2H, NH₂), 3.98 (s, 3H).

Ex. 175: ¹H NMR (400 MHz, DMSO-d6), δ 8.43 (d, 1H), 8.24 (d, 1H), 6.75 (s, 2H), 6.17 (s, 2H), 5.80 (bs, 2H, NH₂), 4.47 (q, 2H), 1.32 (t, 3H).

Ex. 176: ¹H NMR (400 MHz, DMSO-d6), δ 8.43 (d, 1H), 8.25 (d, 1H), 7.28 (s, 1H), 7.00 (s, 1H), 5.84 (bs, 2H, NH₂), 4.48 (q, 2H), 3.85 (s, 3H), 3.75 (s, 3H), 1.33 (t, 3H).

Ex. 177: ¹H NMR (400 MHz, DMSO-d6), δ 8.28 (d, 1H), 8.16 (d, 1H), 6.94 (s, 1H), 6.90 (s, 1H), 6.13 (s, 2H), 5.30 (bs, 2H, NH₂), 4.44 (q, 2H), 2.53 (q, 2H), 1.33 (t, 3H), 1.08 (t, 3H).

Ex. 178: ¹H NMR (400 MHz, DMSO-d6), δ 8.31 (d, 1H), 8.18 (d, 1H), 6.94 (s, 1H), 6.90 (s, 1H), 6.13 (s, 2H), 5.30 (bs, 2H, NH₂), 3.96 (s, 3H), 2.52 (q, 2H), 1.06 (t, 3H).

Ex. 179: ¹H NMR (400 MHz, DMSO-d6), δ 8.45 (d, 1H), 8.27 (d, 1H), 7.81 (s, 1H), 7.66 (s, 1H), 5.85 (bs, 2H, NH₂), 4.29-4.04 (m, 2H), 3.99 (s, 3H).

Ex. 180: ¹H NMR (400 MHz, DMSO-d6), δ 8.48 (d, 1H), 8.28 (d, 1H), 7.51 (s, 1H), 7.46 (s, 1H), 6.00 (bs, 2H, NH₂), 4.22 (q, 2H), 3.99 (s, 3H).

Ex. 181: ¹H NMR (400 MHz, DMSO-d6), δ 8.48 (d, 1H), 8.28 (d, 1H), 7.61-7.64 (d+d, 2H), 5.95 (bs, 2H, NH₂), 4.12-3.96 (m, 2H), 4.00 (s, 3H).

Ex. 182: ¹H NMR (400 MHz, DMSO-d6), δ 8.50 (d, 1H), 8.30 (d, 1H), 7.80 (s, 2H), 6.16 (bs, 2H, NH₂), 4.36-4.14 (m, 2H), 4.00 (s, 3H).

Biological Examples

*Boophilus microplus* (dip)

Test animals: adult engorged *Boophilus microplus* females of the SP-resistant Parkhurst strain Solvent: dimethyl sulphoxide 10 mg of active ingredient are dissolved in 0.5 ml of dimethyl sulphoxide. For the purpose of preparing a suitable formulation, the active ingredient solution is diluted with water to the concentration desired in each case. This active ingredient preparation is pipetted into tubes. 8-10 ticks are transferred into a further tube with holes. The tube is immersed into the active ingredient formulation, and all ticks are completely wetted. After the liquid has run out, the ticks are transferred onto filter discs in plastic dishes and stored in a climate-controlled room. The activity is assessed after 7 days by laying of fertile eggs. Eggs whose fertility is not outwardly visible are stored in glass tubes in a climate-controlled cabinet until the larvae hatch. Efficacy of 100% means that none of the ticks has laid any fertile eggs.

In this test, for example, the following compounds of the Preparation Examples show an efficacy of 90% at an application rate of 100 ppm: Ex. No. 8, 14, 26

In this test, for example, the following compounds of the Preparation Examples show an efficacy of 95% at an application rate of 100 ppm: Ex. No. 22, 133

In this test, for example, the following compounds of the Preparation Examples show an efficacy of 100% at an application rate of 100 ppm: Ex. No. 2, 5, 15, 17, 18, 20, 47, 48, 51, 75, 76, 132

*Boophilus microplus* Test (BOOPMI Injection)

Solvent: dimethyl sulphoxide

To prepare an appropriate active ingredient formulation, 10 mg of active ingredient are mixed with 0.5 ml of solvent and the concentrate is diluted with solvent to the desired concentration. The active ingredient solution is injected into the abdomen (Boophilus microplus), and the animals are transferred into dishes and stored in a climate-controlled room. The efficacy is assessed by laying of fertile eggs. After 7 days, the efficacy in % is determined. 100% means that none of the ticks has laid any fertile eggs.

In this test, for example, the following compounds of the Preparation Examples show an efficacy of 100% at an application rate of 20 µg animal: Ex. No. 2, 3, 5, 6, 8, 9, 10, 12, 14, 15, 17, 18, 20, 21, 22, 26, 28, 46, 47, 48, 51, 75, 76, 89, 131, 132, 133, 135, 136, 139, 141

*Ctenocephalides felis* Test (CTECFE)

Solvent: 1 part by weight of dimethyl sulphoxide

For the purpose of preparing an appropriate active ingredient formulation, 10 mg of active ingredient are mixed with 0.5 ml of dimethyl sulphoxide. A portion of the concentrate is diluted with citrated cow's blood and the desired concentration is established. About 20 unfed adult fleas (*Ctenocephalides felis*) are introduced into a chamber closed at the top and bottom with gauze. A metal cylinder, the bottom of which is closed with Parafilm, is placed onto the chamber. The cylinder contains the blood/active ingredient preparation, which can be imbibed by the fleas through the Parafilm membrane. After 2 days, the kill in % is determined. 100% means that all fleas have been killed; 0% means that none of the fleas have been killed.

In this test, for example, the following compounds of the Preparation Examples show an efficacy of 80% at an application rate of 100 ppm: Ex. No. 41, 46

In this test, for example, the following compounds of the Preparation Examples show an efficacy of 90% at an application rate of 100 ppm: Ex. No. 2, 6, 10, 12, 76

In this test, for example, the following compounds of the Preparation Examples show an efficacy of 95% at an application rate of 100 ppm: Ex. No. 15, 22, 26

In this test, for example, the following compounds of the Preparation Examples show an efficacy of 100% at an application rate of 100 ppm: Ex. No. 14, 17, 47, 48, 51, 75, 89, 131, 132, 133, 135, 136, 139, 141

*Lucilia cuprina* Test (LUCICU)

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration. Vessels containing horse meat treated with the active ingredient preparation of the desired concentration are populated with about 20 Lucilia cuprina larvae.

After 2 days, the kill in % is determined. 100% means that all of the larvae have been killed; 0% means that none of the larvae have been killed.

In this test, for example, the following compounds of the Preparation Examples show an efficacy of 100% at an application rate of 100 ppm: Ex. No. 2, 3, 5, 6, 8, 9, 10, 12, 14, 15, 17, 18, 20, 21, 22, 26, 28, 41, 46, 47, 48, 51, 75, 76, 89, 131, 132, 133, 135, 136, 139, 141

*Musca domestica* Test

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration. Vessels containing a sponge treated with the active ingredient preparation of the desired concentration are populated with adult Musca domestica. After 2 days, the kill in % is determined. 100% means that all of the flies have been killed; 0% means that none of the flies have been killed.

In this test, for example, the following compounds of the Preparation Examples show an efficacy of 80% at an application rate of 20 ppm: Ex. No. 2, 133, 141

In this test, for example, the following compounds of the Preparation Examples show an efficacy of 90% at an application rate of 20 ppm: Ex. No. 14, 48

In this test, for example, the following compounds of the Preparation Examples show an efficacy of 80% at an application rate of 100 ppm: Ex. No. 5, 6, 47, 76, 89, 132

In this test, for example, the following compounds of the Preparation Examples show an efficacy of 95% at an application rate of 100 ppm: Ex. No. 15

In this test, for example, the following compounds of the Preparation Examples show an efficacy of 100% at an application rate of 100 ppm: Ex. No. 10, 12, 17, 21, 75, 131

*Amblyomma hebraeum* Test (AMBYHE)

Solvent: dimethyl sulphoxide

To prepare an appropriate active ingredient formulation, 10 mg of active ingredient are mixed with 0.5 ml of dimethyl sulphoxide and the concentrate is diluted with water to the desired concentration. Tick nymphs (Amblyomma hebraeum) are placed into perforated plastic beakers and immersed in the desired concentration for one minute. The ticks are transferred on filter paper into a Petri dish and stored in a climate-controlled cabinet. After 42 days, the kill in % is determined. 100% means that all of the ticks have been killed; 0% means that none of the ticks have been killed.

In this test, for example, the following compounds of the Preparation Examples show an efficacy of 100% at an application rate of 100 ppm: Ex. No. 48, 76

*Myzus* Test (MYZUPE Spray Treatment)

Solvent: 78 parts by weight of acetone 1.5 parts by weight of dimethylformamide

Emulsifier: 0.5 part by weight of alkylaryl polyglycol ether

To prepare an appropriate active ingredient preparation, 1 part by weight of active ingredient is mixed with the stated amounts of solvent and emulsifier, and the concentrate is diluted with emulsifier-containing water to the desired concentration. Discs of Chinese cabbage (*Brassica pekinensis*) infested by all stages of the green peach aphid (*Myzus persicae*) are sprayed with an active ingredient preparation of the desired concentration. After 6 days, the efficacy in % is determined. 100% means that all of the aphids have been destroyed; 0% means that none of the aphids have been destroyed.

In this test, for example, the following compounds of the Preparation Examples show an efficacy of 80% at an application rate of 500 g/ha: Ex. No. 33, 46, 47, 76, 103

In this test, for example, the following compounds of the Preparation Examples show an efficacy of 90% at an application rate of 500 g/ha: Ex. No. 18, 41, 48, 74

In this test, for example, the following compounds of the Preparation Examples show an efficacy of 100% at an application rate of 500 g/ha: Ex. No. 8, 9, 14, 15, 17, 20, 21, 22, 59, 75, 77, 150, 167, 168, 169, 170, 171, 172, 174, 175

*Phaedon* Test (PHAECO Spray Treatment)

Solvent: 78.0 parts by weight of acetone 1.5 parts by weight of dimethylformamide Emulsifier: 0.5 part by weight of alkylaryl polyglycol ether To prepare an appropriate active ingredient preparation, 1 part by weight of active ingredient is mixed with the stated amounts of solvent and emulsifier, and the concentrate is diluted with emulsifier-containing water to the desired concentration. Discs of Chinese cabbage (Brassica pekinensis) are sprayed with an active ingredient preparation of the desired concentration and, after drying, populated with larvae of the mustard beetle (Phaedon cochleariae). After 7 days, the efficacy in % is determined. 100% means that all beetle larvae have been killed; 0% means that none of the beetle larvae have been killed.

In this test, for example, the following compounds of the Preparation Examples show an efficacy of 83% at an application rate of 500 g/ha: Ex. No. 4, 13, 107

In this test, for example, the following compounds of the Preparation Examples show an efficacy of 100% at an application rate of 500 g/ha: Ex. No. 2, 3, 5, 6, 9, 12, 14, 15, 17, 18, 20, 21, 22, 23, 26, 27, 28, 33, 41, 43, 44, 46, 47, 48, 51, 52, 59, 65, 66, 74, 75, 76, 77, 79, 86, 87, 89, 116, 121, 122, 123, 124, 125, 127, 130, 131, 132, 133, 134, 135, 136, 139, 140, 141, 142, 144, 145, 150, 157, 161, 166, 167, 168, 169, 170, 171, 172, 173, 174, 175

*Spodoptera frugiperda* Test (SPODFR Spray Treatment)

Solvent: 78.0 parts by weight of acetone 1.5 parts by weight of dimethylformamide Emulsifier: 0.5 part by weight of alkylaryl polyglycol ether To prepare an appropriate active ingredient preparation, 1 part by weight of active ingredient is mixed with the stated amounts of solvent and emulsifier, and the concentrate is diluted with emulsifier-containing water to the desired concentration. Discs of maize leaves (*Zea mays*) are sprayed with an active ingredient preparation of the desired concentration and, after drying, populated with caterpillars of the armyworm (*Spodoptera frugiperda*). After 7 days, the efficacy in % is determined. 100% means that all caterpillars have been killed; 0% means that none of the caterpillars have been killed.

In this test, for example, the following compound of the Preparation Examples shows an efficacy of 80% at an application rate of 500 g/ha: 135

In this test, for example, the following compounds of the Preparation Examples show an efficacy of 83% at an application rate of 500 g/ha: Ex. No. 6, 18, 26, 59, 76

In this test, for example, the following compounds of the Preparation Examples show an efficacy of 100% at an application rate of 500 g/ha: Ex. No. 9, 14, 15, 17, 20, 21, 22, 28, 43, 44, 46, 47, 48, 51, 65, 66, 74, 75, 77, 79, 86, 87, 89, 116, 121, 122, 123, 124, 130, 131, 132, 133, 134, 139, 140, 141, 144, 150, 157, 161, 168, 169, 170, 171, 172, 173, 174, 175

*Tetranychus* Test, OP-Resistant (TETRUR Spray Treatment)

Solvent: 78.0 parts by weight of acetone 1.5 parts by weight of dimethylformamide Emulsifier: 0.5 part by weight of alkylaryl polyglycol ether To prepare an appropriate active ingredient preparation, 1 part by weight of active ingredient is mixed with the stated amounts of solvent and emulsifier, and the concentrate is diluted with emulsifier-containing water to the desired concentration. Discs of bean leaves (*Phaseolus vulgaris*) infested by all stages of the red spider mite (*Tetranychus urticae*) are sprayed with an active ingredient preparation of the desired concentration. After 6 days, the efficacy in % is determined. 100% means that all spider mites have been killed; 0% means that none of the spider mites have been killed.

In this test, for example, the following compounds of the Preparation Examples show an efficacy of 80% at an application rate of 500 g/ha: Ex. No. 5, 46, 51, 123, 132, 139

In this test, for example, the following compound of the Preparation Examples shows an efficacy of 80% at an application rate of 100 g/ha: Ex. No. 121

In this test, for example, the following compound of the Preparation Examples shows an efficacy of 90% at an application rate of 100 g/ha: Ex. No. 133

In this test, for example, the following compounds of the Preparation Examples show an efficacy of 90% at an application rate of 500 g/ha: Ex. No. 4, 12, 33, 35, 65, 66, 74, 116, 124, 125, 127, 166, 173

In this test, for example, the following compounds of the Preparation Examples show an efficacy of 100% at an application rate of 500 g/ha: Ex. No. 2, 3, 9, 14, 15, 17, 18, 20, 21, 22, 23, 26, 47, 48, 59, 75, 77, 96, 131, 141, 144, 150, 157, 167, 168, 169, 170, 171, 172, 174, 175

The invention claimed is:

1. A compound of formula (I)

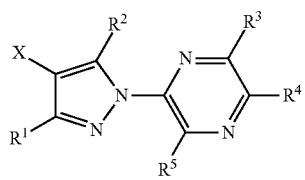

(I)

in which

X is phenyl, 2-pyridyl, or 3-pyridyl, any of which is substituted with one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH=NO—H, —CH=NO-alkyl, —CH=NO-haloalkyl, —C(CH$_3$)=NO—H, —C(CH$_3$)=NO-alkyl, and —C(CH$_3$)=NO-haloalkyl; or phenyl, 2-pyridyl, or 3-pyridyl, any of which is optionally substituted with one or more substituents selected from the group consisting of halogen, cyano, nitro, alkyl, alkoxy, and haloalkyl, where vicinal alkyl, haloalkyl, alkoxy, or haloalkoxy groups on the phenyl, 2-pyridyl, or 3-pyridyl, together with the carbon atoms to which they are bonded, may form a five- or six-membered cyclic system which contains zero, one, or two oxygen or nitrogen atoms, where no two oxygen atoms are directly bonded to one another, and the alkyl is optionally substituted with one or more halogen or alkyl substituents;

$R^1$ is alkyl which is optionally substituted with one or more substituents independently selected from the group consisting of alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl, and cycloalkyl; alkenyl which is optionally substituted with one or more substituents independently selected from the group consisting of halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and cycloalkyl; cycloalkyl which is optionally substituted with one or more substituents independently selected from the group consisting of alkyl, haloalkyl, and halogen; haloalkyl which is optionally substituted with one or more substituents independently selected from the group consisting of alkoxy, alkylsulphanyl, haloalkylsulphanyl, alkylsulphinyl, haloalkylsulphinyl, alkylsulphonyl, haloalkylsulphonyl, and phenyl, wherein the phenyl is optionally substituted with one or more substituents independently selected from the group consisting of halogen, alkyl, haloalkyl, and alkoxy; phenyl which is optionally substituted with one or more substituents independently selected from the group consisting of halogen, alkyl, haloalkyl, and alkoxy; benzyl which is optionally substituted with one or more substituents independently selected from the group consisting of halogen, alkyl, haloalkyl, and alkoxy; cyano; formyl; alkylcarbonyl; —CH=NO—H; —CH=NO-alkyl; —CH=NO-haloalkyl; —C(CH$_3$)=NO—H; —C(CH$_3$) NO-alkyl; or —C(CH$_3$)=NO-haloalkyl;

$R^2$ is amino which is optionally substituted with one or two substituents independently selected from the group consisting of alkyl, haloalkyl, alkoxyalkyl, alkylsulphanylalkyl, alkylsulphinylalkyl, alkylsulphonylalkyl, alkylcarbonyl, cycloalkyl, cycloalkylalkyl, alkenyl, any of which is optionally substituted with halogen, cyano, alkoxy, alkoxycarbonyl or phenyl, where the phenyl is optionally substituted with one or more substituents independently selected from the group consisting of halogen, alkyl, haloalkyl, and alkoxy; alkynyl; alkoxycarbonyl; alkenyloxycarbonyl; alkynyloxycarbonyl; alkoxycarbonylalkyl; alkoxycarbonylcarbonyl; heterocyclyl, heteroaryl, heterocyclylalkyl, or heteroarylalkyl, where the heterocyclic or heteroaromatic ring is optionally substituted with one or more substituents selected independently from the group consisting of halogen, alkyl, haloalkyl, and alkoxy; benzyl or phenylcarbonyl, where the phenyl ring in benzyl or phenylcarbonyl is optionally substituted with one or more substituents selected from the group consisting of halogen, alkyl, haloalkyl, and alkoxy;

$R^3$ and $R^4$ are each independently hydrogen, halogen, alkyl, cycloalkyl, haloalkyl, cyano, hydroxyl, formyl, alkylcarbonyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl, nitro, hydroxyl, SH, alkoxy, alkylsulphanyl, haloalkylsulphanyl, alkylsulphinyl, haloalkylsulphinyl, alkylsulphonyl, or haloalkylsulphonyl;

$R^5$ is halogen, alkyl, haloalkyl, hydroxyl, a.lkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, nitro, amino, alkylamino, dialkylamino, alkylsulphonyamino, dialkylsulphonylamino, formyl, —CH=NO—H, —CH=NO-alkyl, —CH=NO-haloalkyl, —(CH$_3$)=NO—H, —C(CH$_3$)=NO-alkyl, —C(CH$_3$)=NO-haloalkyl, or heteroaryl, where the heteroaromatic ring in the heteroaryl is optionally substituted with one or more substituents selected independently from the group consisting of halogen, alkyl, haloalkyl, and alkoxy; and the N-oxides and salts of the compounds of formula (I).

2. A compound according to claim 1, where

X is phenyl, 2-pyridyl, or 3-pyridyl, any of which is substituted by one or more substituents selected from the group consisting of halogen, alkyl, haloalkyl, alkoxy, haloalkoxy, alkylsulphanyl, haloalkylsulphanyl, alkylsulphinyl, haloalkylsulphinyl, alkylsulphonyl, haloalkylsulphonyl, cyano, nitro, and dialkylamino; or phenyl, 2-pyridyl, or 3-pyridyl, any of which is optionally substituted by one or more substituents selected from the group consisting of halogen, cyano, nitro, alkyl, alkoxy, and haloalkyl, where vicinal alkyl, haloalkyl, or alkoxy groups on the phenyl, 2-pyridyl, or 3-pyridyl, together with the carbon atoms to which they are bonded, may form a five- or six-membered cyclic system which contains zero, one, or two oxygen or nitrogen atoms, Where no two oxygen atoms are directly bonded to one another, and the alkyl is optionally substituted with one or more halogen or alkyl substituents;

$R^1$ is alkyl which is optionally substituted with one or more substituents independently selected from the group consisting of alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl, and cycloalkyl; alkenyl which is optionally substituted with one or more substituents independently selected from the group consisting of halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and cycloalkyl; cycloalkyl which is optionally substituted with one or more substituents independently selected from the group consisting of alkyl, haloalkyl, and halogen; haloalkyl which is optionally substituted with one or more substituents independently selected from the group consisting of alkoxy, alkylsulphanyl, haloalkylsulphanyl, alkylsulphinyl, haloalkylsulphinyl, alkylsulphonyl, haloalkylsulphonyl, phenyl; CH=NOH; CH=NOCH$_3$; or CN;

$R^2$ is amino which is optionally substituted with one or two substituents independently selected from the group consisting of alkyl, haloalkyl, cycloalkylalkyl, alkenyl, alkynyl, heterocyclylalkyl, where the alkenyl, is optionally substituted with halogen or phenyl, and heteroarylalkyl, where the heteroaromatic ring is optionally substituted with one or more substituents selected independently from the group consisting of halogen, alkyl, haloalkyl, and alkoxy; benzyl, where the phenyl ring in the benzyl is optionally substituted with one or more substituents selected independently from the group consisting of halogen, alkyl, haloalkyl, and alkoxy;

$R^3$ and $R^4$ are each independently hydrogen, halogen, alkyl, cycloalkyl, haloalkyl, cyano, or hydroxyl; and $R^5$ is halogen, alkyl, haloalkyl, hydroxyl, alkoxy, haloalkoxy, alkylsulphonyl, haloalkylsulphanyl, alkylsulphinyl, haloalkylsulphinyl, alkylsulphonyl, haloalkylsulphonyl, cyano, amino, alkylamino, dialkylamino, alkylsulphonylamino, dialkylsulphonylamino, or heteroaryl, where the heteroaromatic ring is optionally substituted with one or more substituents selected independently from the group consisting of halogen, alkyl, haloalkyl, and alkoxy.

3. A compound according to claim 1, wherein

X is phenyl, 2-pyridyl, or 3-pyridyl, any of which is substituted by one or more substituents selected from the group consisting of fluorine, chlorine, bromine, iodine, CF$_3$, methoxy, ethoxy, propanyloxy, trifluoroethoxy, methylsulphanyl, 2,2,2-trifluoroethylsulphanyl, methylsulphinyl, 2,2,2-trifluoroethylsulphinyl, methylsulphonyl, 2,2,2-trifluoroethylsulphonyl, cyano, and dimethylamino; or phenyl, which is optionally substituted by one or more substituents selected from the group consisting of halogen, cyano, nitro, methyl, methoxy, or CF$_3$, where vicinal methyl or methoxy groups on the phenyl, together with the carbon atoms to which they are bonded, may form a five- or six-membered cyclic system which contains 1 or 2 oxygen, where no two oxygen atoms are directly bonded to one another, and the methyl is optionally substituted by one or more alkyl radicals;

$R^1$ is CH$_3$, CH$_2$CH$_3$, CH(CH$_3$)$_2$, CH$_2$CH$_3$CH$_3$, C(CH$_3$)$_3$, C(OCH$_3$)HCH$_2$CH$_3$, CH(OCH$_3$)$_2$, CH=CH$_2$, prop-1-en-2-yl, cyclopropyl, CF$_3$, CHFCH$_3$, CHF$_2$, CF$_2$Cl, CF$_2$Br, CF$_2$CF$_3$, CF$_2$CH$_3$, CF$_2$CF$_2$CF$_3$, CF$_2$CF$_2$H, 2-fluoropropan-2-yl, 1,1,2,2-tetrafluoro-2-methoxyethyl, CH=NOH, CH=NOCH$_3$, or CN;

$R^2$ is amino, methylamino, dimethylamino, benzylamino, dibenzylamino, (4-chlorobenzyl)amino, bis(4-chlorobenzyl)amino, (4-methoxybenzyl)amino, bis(4-methoxybenzyl)amino, (2-methylprop-2-en-1-yl)amino, prop-2-en-1-ylamino, diprop-2-en-1-ylamino, bis(2-methylprop-2-en-1-yl)amino, prop-2-yn-1-ylamino, bis(prop-2-yn-1-yl)amino, (pyrazin-2-ylmethyl)amino, (6-methylpyridin-2-ylmethyl)amino, bis(6-methyl-pyridin-2-ylmethyl)amino, or (pyridin-2-ylmethyl)amino;

$R^3$ and $R^4$ are each independently hydrogen, chlorine, or methyl; and $R^5$ is chlorine, bromine, methyl, CF$_3$, methoxy, ethoxy, propoxy, propan-2-yloxy, dimethylamino, cyano, methylsulphanyl, methylsulphonyl, methylsulphonyl, 1H-pyrazol-1-yl, 1H-imidazol-1-yl, or 4-fluoro-1H-pyrazol-1-yl.

4. A composition, comprising at least one compound of the formula (I) according to claim 1.

5. A method for controlling animal pests, comprising allowing one or more compounds of the formula (I) according to claim 1 to act on animal pests, their habitat, seed material, or combinations thereof.

6. A composition comprising at least one compound of the formula (I) according to claim 1, further comprising an extender, a surfactant, or combinations thereof.

7. A compound as claimed in claim 1, of formula (IA):

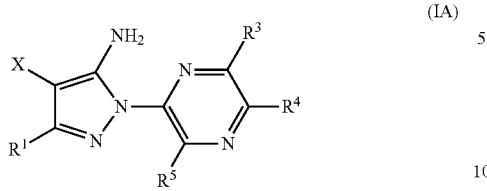

wherein X, $R^1$, $R^3$, $R^4$, and $R^5$ are each as defined in claim 1.

8. A compound as claimed in claim 1, of formula (IB):

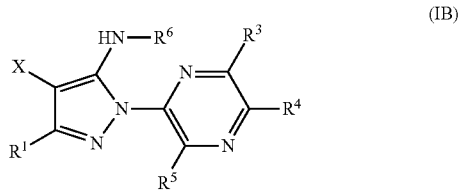

wherein X, $R^1$, $R^3$, $R^4$, and $R^5$ are each as defined in claim 1; and $R^6$ is alkyl; haloalkyl; alkoxyalkyl; alkylsulphanylalkyl; alkylsulphinylalkyl; alkylsulphonylalkyl; alkylcarbonyl; cycloalkyl; cycloalkylalkyl; alkenyl, which is optionally substituted with one or more substituents selected from the group consisting of halogen, cyano, alkoxy, alkoxycarbonyl, and phenyl, where the phenyl ring is optionally substituted with one or more substituents independently selected from the group consisting of halogen, alkyl, haloalkyl, and alkoxy; alkynyl; alkoxycarbonyl; alkenyloxycarbonyl; alkynyloxycarbonyl; alkoxycarbonylalkyl; alkoxycarbonylcarbonyl; heterocyclylalkyl or heteroarylalkyl, any of which is optionally substituted with one or more substituents independently selected from the group consisting of halogen, alkyl, haloalkyl, and alkoxy; benzyl, or phenylcarbonyl, where the phenyl ring in the benzyl or phenylcarbonyl is optionally substituted with one or more substituents independently selected from the group consisting of halogen, alkyl, haloalkyl, and alkoxy.

9. A compound as claimed in claim 1, of formula (IC):

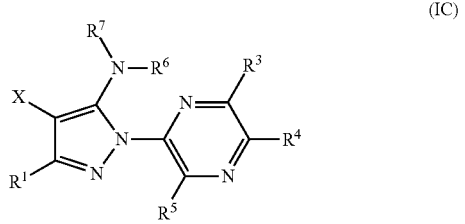

wherein X, $R^1$, $R^3$, $R^4$, and $R^5$ are each as defined in claim; and $R^6$ and $R^7$ are each independently alkyl; haloalkyl; alkoxyalkyl; alkylsulphanylalkyl; alkylsulphinylalkyl; alkylsulphonylalkyl; alkylcarbonyl; cycloalkyl; cycloalkylalkyl; alkenyl, which is optionally substituted with one or more substituents selected from the group consisting of halogen, cyano, alkoxy, alkoxycarbonyl, and phenyl, where the phenyl ring is optionally substituted with one or more substituents independently selected from the group consisting of halogen, alkyl, haloalkyl, and alkoxy; alkynyl; alkoxycarbonyl; alkenyloxycarbonyl; alkynyloxycarbonyl; alkoxycarbonylalkyl; alkoxycarbonylcarbonyl; heterocyclylalkyl or heteroarylalkyl, any of which is optionally substituted with one or more substituents independently selected from the group consisting of halogen, alkyl, haloalkyl, and alkoxy; benzyl, or phenylcarbonyl, where the phenyl ring in the benzyl or phenylcarbonyl is optionally substituted with one or more substituents independently selected from the group consisting of halogen, alkyl, haloalkyl, and alkoxy.

10. A process for preparing a compound of formula (IA) as claimed in claim 7, comprising reacting (a) a compound of formula (III)

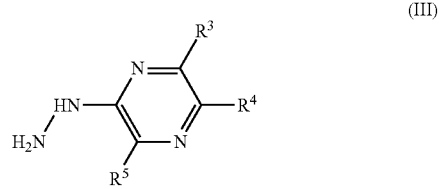

wherein $R^3$ and $R^4$ are each independently hydrogen, halogen, alkyl, cycloalkyl, haloalkyl, cyano, hydroxyl, formyl, alkylcarbonyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl, nitro, hydroxyl, SH, alkoxy, alkylsulphanyl, haloalkylsulphanyl, alkylsulphinyl, haloalkylsulphinyl, alkylsulphonyl or haloalkylsulphonyl; and $R^5$ is halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, —SH, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, nitro, amino, alkylamino, dialkylamino, alkylsulphonylamino, dialkylsulphonylamino, formyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl, or heteroaryl, where the heteroaromatic ring in the heteroaryl is optionally substituted with one or more substituents independently selected from the group consisting of halogen, alkyl, haloalkyl, and alkoxy;

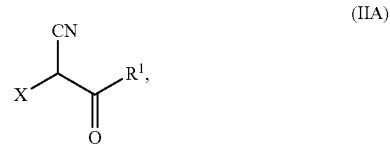

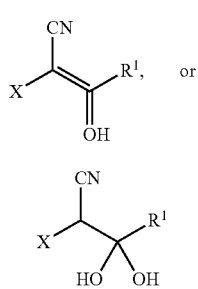

(b) with a compound of one of formula (IIA), (IIB) or (IIC) wherein

X is phenyl, 2-pyridyl, or 3-pyridyl, any of which is substituted with one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsuphanyl, haloalkylsulphanyl, alkylsulphinyl, haioalkylsulphinyl, alkylsulphonyl, haloalkylsulphonyl, cyano, nitro, alkylcarbonyl, alkoxycarhonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH═NO—H, —CH═NO-alkly, —CH═NO-haloalkyl, —C(CH₃)═NO—H, —C(CH₃)═NO-alkyl, and —C(CH₃)═NO-haloalkyl; or phenyl, 2-pyridyi, or 3-pyridyl, any of which is optionally substituted with one or more substituents selected from the group consisting of halogen, cyano, nitro, alkyl, alkoxy, and haloalkyl, where vicinal alky, haloalkyl, alkoxy, or haloalkoxy groups on the phenyl, 2-pyridyl, or 3-pyridyl, together with the carbon atoms to which they are bonded, may form a five- or six-membered cyclic system which contains zero, one, or two oxygen or nitrogen atoms, where no two oxygen atoms are directly bonded to one another, and the alkyl is optionally substituted with one or more halogen or alkyl substituents; and R¹ is alkyl which is optionally substituted with one or more substituents independently selected from the group consisting of alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl, and cycloalkyl; alkenyl which is optionally substituted with one or more substituents independently selected from the group consisting of halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and cycloalkyl; cycloalkyl which is optionally substituted with one or more substituents independently selected from the group consisting of alkyl, haloalkyl, and halogen; haloalkyl which is optionally substituted with one or more substituents independently selected from the group consisting of alkoxy, alkylsulphanyl, haloalkylsulphanyl, alkylsulphinyl, haloalkylsulphinyl, alkylsulphonyl, haloalkylsulphonyl, and phenyl, wherein the phenyl is optionally substituted with one or more substituents independently selected from the group consisting of halogen, alkyl, haloalkyl, and alkoxy; phenyl which is optionally substituted with one or more substituents independently selected from the group consisting of halogen, alkyl, haloalkyl, and alkoxy; benzyl which is optionally substituted with one or more substituents independently selected from the group consisting of halogen, alkyl, haloalkyl, and alkoxy; cyano; formyl; alkylcarbonyl; —CH═NO—H; —CH═NO-alkyl; —CH═NO-aloalkyl; —C(CH₃)═NO—H; —C(CH₃)═NO-alkyl; or —C(CH₃)═NO-haloalkyl.

11. A process for preparing a compound of formula (IA) as claimed in claim 7, comprising reacting

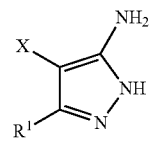

(a) a compound of formula (V) wherein

X is phenyl, 2-pyridyl, or 2-pyridyl, any of which is substituted with one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, halo alkylsulphanyl, alkylsulphinyl, halo alkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH═NO—H, —CH═NO-alkyl, —CH═NO-haloalkyl, —C(CH₃)═NO—H, —C(CH₃)═NO-alkyl, and —C(CH₃)═NO-haloalkyl; or phenyl, 2-pyridyl, or 3-pyridyl, any of which is optionally substituted with one or more substituents selected from the group consisting of halogen, cyano, nitro, alkyl, alkoxy, and haloalkyl, where vicinal alkyl, haloalkyl, alkoxy, or haloalkoxy groups on the phenyl, 2-pyridyl, or 3-pyridyl, together with the carbon atoms to which they are bonded, may form a five- or six-membered cyclic system which contains zero, one, or two oxygen or nitrogen atoms, where no two oxygen atoms are directly bonded to one another, and the alkyl is optionally substituted with one or more halogen or alkyl substituents; and R¹ is alkyl which is optionally substituted with one or more substituents independently selected from the group consisting of alkoxy, haloalkoxy, alkylsulphanyl, haloalkylsulphonyl, alkylsulphinyl, haloalkylsuiphinyl, alkylsulphonyl, haloalkylsulphonyl, alkylcarbonyl, alkoxycarbonyl, hydroxyl, and cycloalkyl; alkenyl which is optionally substituted with one or more substituents independently selected from the group consisting of halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and cycloalkyl; cycloalkyl which is optionally substituted with one or more substituents independently selected from the group consisting of alkyl, haloalkyl, and halogen; haloalkyl which is optionally substituted with one or more substituents independently selected from the group consisting of alkoxy, alkylsulphanyl, haloalkylsulphanyl, alkylsulphinyl, haloalkylsulphinyl, alkylsulphonyl, haloalkylsulphonyl, and phenyl, wherein the phenyl is optionally substituted with one or more substituents independently selected from the group consisting of halogen, alkyl, haloalkyl, and alkoxy; phenyl which is optionally substituted with one or more substituents independently selected from the group consisting of halogen, alkyl, haloalkyl, and alkoxy; benzyl which is optionally substituted with one or more substituents independently selected from the group consisting of halogen, alkyl, haloalkyl, and alkoxy; cyano; formyl; alkylcarbonyl; —CH=NO—H; —CH=NO-alkyl; —CH=NO-haloalkyl; —C(CH₃)=NO—H; —C(CH₃)=NO-alkyl; or —C(CH₃)=NO-haloalkyl;

(b) with a compound of formula (VI)

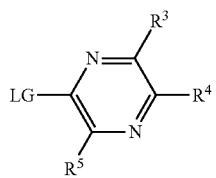

(VI)

wherein

LG is halogen or alkylsulphonyl;

$R^3$ and $R^4$ are each independently hydrogen, halogen, alkyl, cycloalkyl, haloalkyl, cyano, hydroxyl, formyl, alkylcarbonyl, —CH=NO—H, —CH=NO-alkyl, —CH=NO-haloalkyl, —C(CH₃)=NO—H, —C(CH₃)=NO-alkyl, —C(CH₃)=NO-haloalkyl, nitro, hydroxyl, SH, alkoxy, alkylsulphanyl, haloalkylsulphanyl, alkylsulphinyl, haloalkylsulphinyl, alkylsulphonyl or haloalkylsulphonyl; and $R^5$ is halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, —SH, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, nitro, amino, alkylammo, dialkylamino, alkylsulphonylamino, dialkylsulphonylamino, formyl, —CH=NO—H, —CH=NO-alkyl, —CH=NO-haloalkyl, —C(CH₃)=NO—H, —C(CH₃)=NO-alkyl, —C(CH₃)NO-haloalkyl, or heteroaryl, where the heteroaromatic ring in the heteroaryl is optionally substituted with one or more substituents independently selected from the group consisting of halogen, alkyl, haloalkyl, and alkoxy.

12. A process for preparing a compound of formula (IA) as claimed in claim 7, comprising reacting (a) a compound of formula (III)

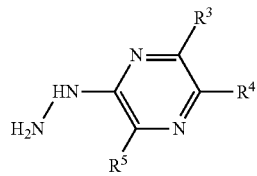

(III)

wherein $R^3$ and $R^4$ are each independently hydrogen, halogen, alkyl, cycloalkyl, haloalkyl, cyano, hydroxyl, formyl, alkylcarbonyl, —CH=NO—H, —CH=NO-alkyl, —CH=NO-haloalkyl, —C(CH₃)=NO—H, —C(CH₃)=NO-alkyl, —C(CH₃)=NO-haloalkyl, nitro, hydroxyl, SH, alkoxy, alkylsulphanyl, haloalkylsulphanyl, alkylsulphinyl, haloalkylsulphinyl, alkylsulphonyl, or haloalkylsulphonyl; and $R^5$ is halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, —SH, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, nitro, amino, alkylamino, dialkylamino, alkylsulphonylamino, dialkylsulphonylamino, formyl, —CH=NO—H, —CH=NO-alkly, —CH=NO-haloalkyl, —C(CH₃)=NO—H, —C(CH₃)=NO-alkyl, —C(CH₃)=NO-haloalkyl, or heteroaryl, where the heteroaromatic ring in the heteroaryl is optionally substituted with one or more substituents independently selected from the group consisting of halogen, alkyl, haloalkyl, and alkoxy;

(b) with a compound of formula (VII)

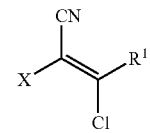

(VII)

wherein

X is phenyl, 2-pyridyl, or 3-pyridyl, any of which is substituted with one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, Laloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH=NO—H, —CH=NO-alkyl, —CH=NO-haloalkyl, —C(CH₃)=NO—H, —C(CH₃)=NO-alkyl, and —C(CH₃)=NO-haloalkyl; or phenyl, 2-pyridyl, or 3-pyridyl, any of which is optionally substituted with one or more substituents selected from the group consisting of halogen, cyano, nitro, alkyl, alkoxy, and haloalkyl, where vicinal alkyl, haloalkyl, alkoxy, or haloalkoxy groups on the phenyl, 2-pyridyl, or 3-pyridyl, together with the carbon atoms to which they are bonded, may form a five- or six-membered cyclic system which contains zero, one, or two oxygen or nitrogen atoms, where no two oxygen atoms are directly bonded to one another, and the alkyl is optionally substituted with one or more halogen or alkyl substituents; and $R^1$ is alkyl which is optionally substituted with one or more substituents independently selected from the group consisting of alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl, and cycloalkyl; alkenyl which is optionally substituted with one or more substituents independently selected from the group consisting of halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and cycloalkyl; cycloalkyl which is optionally substituted with one or more substituents independently selected from the group consisting of alkyl, haloalkyl, and halogen; haloalkyl which is optionally substituted with one or more substituents independently selected from the group consisting of alkoxy, alkylsulphanyl, haloalkylsulphanyl, alkylsulphinyl, halo alkylsulphinyl, alkylsulphonyl, haloalkylsulphonyl, and phenyl, wherein the phenyl is optionally substituted with one or more substituents independently selected from the group consisting of halogen, alkyl, haloalkyl, and alkoxy; phenyl which is optionally substituted with one or more substituents independently selected from the group consisting of halogen, alkyl, haloalkyl, and alkoxy; benzyl which is optionally substituted with one or more substituents independently selected from the group consisting of halogen, alkyl, haloalkyl, and alkoxy; cyano; formyl; alkylcarbonyl; —CH=NO—H; —CH=NO-alkyl; —CH=NO-haloalkyl; —C(CH₃)=NO—H; —C(CH₃)=NO-alkyl; or —C(CH)=NO-haloalkyl.

13. A process for preparing a compound of formula (IB) as claimed in claim 8, comprising reacting
(a) a compound of formula (IA)

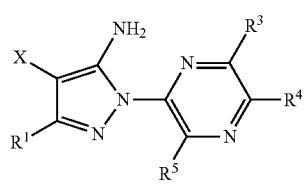

(IA)

wherein
X is phenyl, 2-pyridyl, or 3-pyridyl, any of which is substituted with one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, amino, alkylamino, dialkylamino, alkylsulphonylamino, dialkylsulphonylamino, formyl, —CH=NO—H, —CH=NO-alkyl, —CH=NO-haloalkyl, —C(CH₃)=NO—H, —C(CH₃)=NO-alkyl, and —C(CH₃)=NO-haloalkyl; or
phenyl, 2-pyridyl, or 3-pyridyl, any of which is optionally substituted with one or more substituents selected from the group consisting of halogen, cyano, nitro, alkyl, alkoxy, and haloalkyl, where vicinal alkyl, haloalkyl, alkoxy, or haloalkoxy groups on the phenyl, 2-pyridyl, or 3-pyridyl, together with the carbon atoms to which they are bonded, may form a five- or six-membered cyclic system which contains zero, one, or two oxygen or nitrogen atoms, where no two oxygen atoms are directly bonded to one another, and the alkyl is optionally substituted with one or more halogen or alkyl substituents;

R¹ is alkyl which is optionally substituted with one or more substituents independently selected from the group consisting of alkoxy, haloalkoxy, alkylsulphanyl, halo alkylsulphanyl, alkylsulphinyl, haloalkylsulphinyl, alkylsulphonyl, haloalkylsulphonyl, alkylcarbonyl, alkoxycarbonyl, hydroxyl, and cycloalkyl; alkenyl which is optionally substituted with one or more substituents independently selected from the group consisting of halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and cycloalkyl; cycloalkyl which is optionally substituted with one or more substituents independently selected from the group consisting of alkyl, haloalkyl, and halogen; haloalkyl which is optionally substituted with one or more substituents independently selected from the group consisting of alkoxy, alkylsulphanyl, haloalkylsulphanyl, alkylsulphinyl, haloalkylsulphinyl, alkylsulphonyl, haloalkylsulphonyl, and phenyl, wherein the phenyl is optionally substituted with one or more substituents independently selected from the group consisting of halogen, alkyl, haloalkyl, and alkoxy; phenyl which is optionally substituted with one or more substituents independently selected from the group consisting of halogen, alkyl, haloalkyl, and alkoxy; benzyl which is optionally substituted with one or more substituents independently selected from the group consisting of halogen, alkyl, haloalkyl, and alkoxy; cyano; formyl; alkylcarbonyl; —CH=NO—H; —CH=NO-alkyl; —CH=NO-haloalkyl; —C(CH₃)=NO—H; —C(CH₃ )=NO-alkyl; or —C(CH₃)=NO-haloalkyl;

R³ and R⁴ are each independently hydrogen, halogen, alkyl, cycloalkyl, haloalkyl, cyano, hydroxyl, formyl, alkylcarbonyl, —CH=NO—H, —CH=NO-alkyl, —CH=NO-haloalkyl, —C(CH₃)=NO—H, —C(CH₃)=NO-alkyl, —C(CH₃)=NO-haloalkyl, nitro, hydroxyl, SH, alkoxy, alkylsulphanyl, haloalkylsulphanyl, alkylsulphinyl, haloalkylsulphinyl, alkylsulphonyl, or haloalkylsulphonyl; and R⁵ is halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, -SH, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, dialkylcarboxamide, trialkylsilyl, nitro, amino, alkylamino, dialkylamino, alkylsulphonylamino, dialkylsulphonylamino, formyl, —CH=NO—H, —CH=NO-alkyl, —CH=NO-haloalkyl, —C(CH₃)=NO—H, —C(CH₃)=NO-alkyl, —C(CH₃)=NO-haloalkyl, or heteroaryl, where the heteroaromatic ring in the heteroaryl is optionally substituted with one or more substituents independently selected from the group consisting of halogen, alkyl, haloalkyl, and alkoxy;

(b) with a compound R⁶-LG
wherein
LG is halogen or alkylsulphonyl; and
R⁶ is alkyl; haloalkyl; alkoxyalkyl; alkylsulphanylalkyl; alkylsulphinylalkyl; alkylsulphonylalkyl; alkylcarbonyl; cycloalkyl; cycloalkylalkyl; alkenyl, which is optionally substituted with one or more substituents selected from the group consisting of halogen, cyano, alkoxy, alkoxycarbonyl, and phenyl, where the phenyl ring is optionally substituted with one or more substituents independently selected from the group consisting of halogen, alkyl, haloalkyl, and alkoxy; alkynyl; alkoxycarbonyl; alkenyloxycarbonyl; alkynyloxycarbonyl; alkoxycarbonylalkyl; alkoxycarbonylcarbonyl; heterocyclylalkyl or heteroarylalkyl, any of which is optionally substituted with one or more substituents independently selected from the group consisting of halogen, alkyl, haloalkyl, and alkoxy; benzyl or phenylcarbonyl, where the phenyl ring in benzyl or phenylcarbonyl is optionally substituted with one or more substituents independently selected from the group consisting of halogen, alkyl, haloalkyl, and alkoxy.

14. A process for preparing a compound of formula (IC) as claimed in claim 9, comprising reacting
(a) a compound of formula (IA)

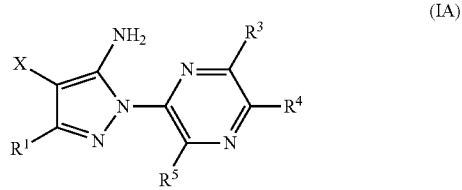

(IA)

wherein
X is phenyl, 2-pyridyl, or 3-pyridyl, any of which is substituted with one or more substituents selected from the group consisting of halogen, alkyl, haloalkyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, alkylsulphanyl, haloalkylsulphanyl, alkylsulphinyl, haloalkylsulphinyl, alkylsulphonyl, haloalkylsulphonyl, cyano, nitro, alkylcarbonyl, alkoxycarbonyl, alkoxycarbonylalkyl, carboxyl, carboxamide, di alkylcarboxamide, trialkylsilyl, amino, alkylamino, dialkylamino, alkylsulphonylamino, dialkylsulphonylamino, formyl, —CH=NO—H, —CH=NO-alkyl, —CH=NO-haloalkyl, —C(CH$_3$)=NO—H, —C(CH$_3$)=NO-alkyl, and —C(CH$_3$)=NO-haloalkyl; or
phenyl, 2-pyridyl, or 3-pyridyl, any of which is optionally substituted with one or more substituents selected from the group consisting of halogen, cyano, nitro, alkyl, alkoxy, and haloalkyl, where vicinal alkyl, haloalkyl, alkoxy, or haloalkoxy groups on the phenyl, 2-pyridyl, or 3-pyridyl, together with the carbon atoms to which they are bonded, may form a five- or six-membered cyclic system which contains zero, one, or two oxygen or nitrogen atoms, where no two oxygen atoms are directly bonded to one another, and the alkyl is optionally substituted with one or more halogen or alkyl substituents;
$R^1$ is alkyl which is optionally substituted with one or more substituents independently selected from the group consisting of alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, hydroxyl, and cycloalkyl; alkenyl which is optionally substituted with one or more substituents independently selected from the group consisting of halogen, alkoxy, haloalkoxy, alkylsulphanyl, haloalkylsulphanyl, alkylsulphinyl, haloalkylsulphinyl, alkylsulphonyl, haloalkylsulphonyl, alkylcarbonyl, alkoxycarbonyl, and cycloalkyl; cycloalkyl which is optionally substituted with one or more substituents independently selected from the group consisting of alkyl, haloalkyl, and halogen; haloalkyl which is optionally substituted with one or more substituents independently selected from the group consisting of alkoxy, alkylsulphanyl, haloalkylsulphanyl, alkylsulphinyl, haloalkylsulphinyl, alkylsulphonyl, haloalkylsulphonyl, and phenyl, wherein the phenyl is optionally substituted with one or more substituents independently selected from the group consisting of halogen, alkyl, haloalkyl, and alkoxy; phenyl which is optionally substituted with one or more substituents independently selected from the group consisting of halogen, alkyl, haloalkyl, and alkoxy; benzyl which is optionally substituted with one or more substituents independently selected from the group consisting of halogen, alkyl, haloalkyl, and alkoxy; cyano; formyl; alkylcarbonyl; —CH=NO—H; —CH=NO-alkyl; —CH=NO-haloalkyl; —C(CH$_3$)=NO—H; —C(CH$_3$)=NO-alkyl; or —C(CH$_3$)=NO-haloalkyl;
$R^3$ and $R^4$ are each independently hydrogen, halogen, alkyl, cycloalkyl, haloalkyl, cyano, hydroxyl, formyl, alkylcarbonyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl, nitro, hydroxyl, SH, alkoxy, alkylsulphanyl, haloalkylsulphanyl, alkylsulphinyl, haloalkylsulphinyl, alkylsulphonyl, or haloalkylsulphonyl; and
$R^5$ is halogen, alkyl, haloalkyl, hydroxyl, alkoxy, alkoxyalkyl, alkoxyalkoxy, cycloalkyl, alkenyloxy, alkynyloxy, benzyloxy, cycloalkylalkoxy, haloalkoxy, haloalkoxyalkyl, —SH, alkylsulphanyl, haloalkylsulphanyl, alkylsulphinyl, haloalkylsulphinyl, alkylsulphonyl, haloalkylsulphonyl, cyano, nitro, aikyicarbonyl, alkoxycarbonyl, alkoxycarbonylalkyl, carboxyl, carboxamide, dialkylcarboxamide, trialkylsilyl, nitro, amino, alkylamino, dialkylamino, alkylsulphonylamino, dialkylsulphonylamino, formyl, —CH=NO—H, —CH=NO-alkyl, —CH=NO-haloalkyl, —C(CH$_3$)=NO—H, —C(CH$_3$)=NO-alkyl, —C(CH$_3$)=NO-haloalkyl, or heteroaryl, where the heteroaromatic ring in the heteroaryl is optionally substituted with one or more substituents independently selected from the group consisting of halogen, alkyl, haloalkyl, and alkoxy;
(b) with a compound $R^6$-LG
wherein
LG is halogen or alkylsulphonyl; and
$R^6$ is alkyl; haloalkyl; alkoxyalkyl; alkylsulphanylalkyl; alkylsulphinylalkyl; alkylsulphonylalkyl; alkylcarbonyl; cycloalkyl; cycloalkylalkyl; alkenyl, which is optionally substituted with one or more substituents selected from the group consisting of halogen, cyano, alkoxy, alkoxycarbonyl, and phenyl, where the phenyl ring is optionally substituted with one or more substituents independently selected from the group consisting of halogen, alkyl, haloalkyl, and alkoxy; alkynyl; alkoxycarbonyl; alkenyloxycarbonyl; alkynyloxycarbonyl; alkoxycarbonylalkyl; alkoxycarbonylcarbonyl; heterocyclylalkyl or heteroarylalkyl, any of which is optionally substituted with one or more substituents independently selected from the group consisting of halogen, alkyl, haloalkyl, and alkoxy; benzyl or phenylcarbonyl, where the phenyl ring in benzyl or phenylcarbonyl is optionally substituted with one or more substituents independently selected from the group consisting of halogen, alkyl, haloalkyl, and alkoxy; and
(c) a compound of formula $R^7$-LG
wherein
LG is halogen of alkylsulphonyl; and
$R^7$ is alkyl; haloalkyl; alkoxyalkyl; alkylsulphanylalkyl; alkylsulphinylalkyl;
alkylsulphonylalkyl; alkylcarbonyl; cycloalkyl; cycloalkylalkyl; alkenyl, which is optionally substituted with one or more substituents selected from the group consisting of halogen, cyano, alkoxy, alkoxycarbonyl, and phenyl, where the phenyl ring is optionally substituted with one or more substituents independently selected from the group consisting of halogen, alkyl, haloalkyl, and alkoxy; alkynyl; alkoxycarbonyl; alkenyloxycarbonyl; alkynyloxycarbonyl; alkoxycarbonylalkyl; alkoxycarbonylcarbonyl; heterocyclylalkyl, or heteroarylalkyl, any of which is optionally substituted with one or more substituents independently selected from the group consisting of halogen, alkyl, haloalkyl, and alkoxy; benzyl or phenylcarbonyl, where the phenyl ring in benzyl or phenylcarbonyl is optionally substituted with one or more substituents independently selected from the group consisting of halogen, alkyl, haloalkyl, and alkoxy.

15. A compound according to claim 1, selected from the group consisting of:

1-(3-methoxypyrazin-2-yl)-4-[3-chloro-5-(trifluoromethyephenyl]-3-chloro(difluoro)methyl-1H-pyrazol-5-amine;

1-(3-methoxypyrazin-2-yl)-4-[3-fluoro-5-(trifluoromethyl)phenyl]-3-pentafluoroethyl-1H-pyrazol-5-amine;

1-(3-methoxypyrazin-2-yl)-4-F-chloro-5-(trifluoromethyl)phenylj-3-(1,1,2,2,-tetrafluoro-2-methoxyethyl)-1H-pyrazol-5-amine;

1-(3-methoxypyrazin-2-yl)-4-[7-chloro-1,3-benzodioxol-5-yl]-3-trifluoromethyl-1H-pyrazol-5-amine;

1-(3-methoxypyrazin-2-yl)-4-[7-chloro-1,3-benzodioxol-5-yl]-3-methyl-1H-pyrazol-5-amine; and 1-(3-methoxypyrazin-2-yl)-4-[9-bromo-3,4-dihydro-2H-1,5-benzodioxepin-7-yl]-3-trifluoromethyl-1H-pyrazol-5-amine.

16. A compound according to claim 1, which is 1-(3-methoxypyrazin-2-yl)-4-[7-bromo-1,3-benzodioxol-5-yl]-3-trifluoromethyl-1H-pyrazol-5-mine.

* * * * *